US012357289B2

(12) United States Patent
Subramaniam et al.

(10) Patent No.: US 12,357,289 B2
(45) Date of Patent: Jul. 15, 2025

(54) SUTURE RETENTION DEVICE

(71) Applicant: DRS Vascular, Inc., San Jose, CA (US)

(72) Inventors: Raj Subramaniam, Fremont, CA (US); Robert Quintos, Newark, CA (US); Shashank Raina, Santa Clara, CA (US)

(73) Assignee: DRS Vascular, Inc., San Jose, CA (US)

( * ) Notice: Subject to any disclaimer, the term of this patent is extended or adjusted under 35 U.S.C. 154(b) by 0 days.

(21) Appl. No.: 18/965,484

(22) Filed: Dec. 2, 2024

(65) Prior Publication Data
US 2025/0090155 A1 Mar. 20, 2025

Related U.S. Application Data

(62) Division of application No. 18/455,382, filed on Aug. 24, 2023, now Pat. No. 12,185,929.

(60) Provisional application No. 63/453,020, filed on Mar. 17, 2023.

(51) Int. Cl.
*A61B 17/00* (2006.01)
*A61B 17/04* (2006.01)

(52) U.S. Cl.
CPC ...... *A61B 17/0057* (2013.01); *A61B 17/0487* (2013.01); *A61B 2017/00623* (2013.01); *A61B 2017/00663* (2013.01); *A61B 2017/0448* (2013.01); *A61B 2017/0456* (2013.01); *A61B 2017/0459* (2013.01)

(58) Field of Classification Search
CPC ...... A61B 17/0487; A61B 2017/00623; A61B 2017/00663; A61B 2017/0448; A61B 2017/0456; A61B 2017/0459
See application file for complete search history.

(56) References Cited

U.S. PATENT DOCUMENTS

| 4,453,292 A | 6/1984 | Bakker |
| 5,391,182 A * | 2/1995 | Chin ............... A61B 17/0469 |
| | | 604/15 |
| 5,451,082 A | 9/1995 | Murai |
| 5,514,159 A | 5/1996 | Matula et al. |

(Continued)

FOREIGN PATENT DOCUMENTS

| WO | WO-2013188351 A2 | 12/2013 |
| WO | WO-2022143990 A1 | 7/2022 |
| WO | 2024196425 | 9/2024 |

OTHER PUBLICATIONS

"U.S. Appl. No. 18/455,382, Preliminary Amendment filed May 28, 2024", 8 pgs.

(Continued)

*Primary Examiner* — Alexander J Orkin
(74) *Attorney, Agent, or Firm* — Schwegman Lundberg & Woessner, P.A.

(57) ABSTRACT

A suture retention device includes a housing having one or more suture slots. The device also includes a plunger with suture slots. The plunger is slidably disposed in a channel in the housing and when the housing suture slots are aligned with the plunger suture slots, a suture filament may be disposed in the slots. When the plunger is actuated so that the housing suture slots are misaligned with the plunger suture slots, the suture filament is captured between the plunger and the housing preventing movement of the suture filament.

11 Claims, 32 Drawing Sheets

(56) References Cited

U.S. PATENT DOCUMENTS

| | | | |
|---|---|---|---|
| 5,954,732 A * | 9/1999 | Hart | A61B 17/0469 |
| | | | 606/144 |
| 9,017,296 B2 | 4/2015 | Beck et al. | |
| 9,119,614 B2 | 9/2015 | Gadladge | |
| 2005/0004602 A1 | 1/2005 | Hart et al. | |
| 2005/0192629 A1* | 9/2005 | Saadat | A61F 5/0076 |
| | | | 606/221 |
| 2006/0047314 A1 | 3/2006 | Green | |
| 2006/0184201 A1 | 8/2006 | James | |
| 2008/0275474 A1 | 11/2008 | Martin et al. | |
| 2009/0062743 A1 | 3/2009 | Rotella et al. | |
| 2011/0152889 A1 | 6/2011 | Ashland | |
| 2012/0226310 A1 | 9/2012 | Frankland et al. | |
| 2014/0163615 A1 | 6/2014 | Gadlage et al. | |
| 2017/0014122 A1 | 1/2017 | Lear | |
| 2017/0095246 A1 | 4/2017 | Mcghie | |
| 2018/0214598 A1 | 8/2018 | Stasko et al. | |
| 2022/0142638 A1 | 5/2022 | Enright et al. | |
| 2024/0307045 A1 | 9/2024 | Subramaniam et al. | |

OTHER PUBLICATIONS

"U.S. Appl. No. 18/455,382, Notice of Allowance mailed Sep. 3, 2024", 12 pgs.
"International Application Serial No. PCT/US2023/072837, International Search Report mailed Feb. 8, 2024", 2 pgs.
"International Application Serial No. PCT/US2023/072837, Written Opinion mailed Feb. 8, 2024", 11 pgs.

* cited by examiner

SUTURE RETENTION DEVICE

CLAIM OF PRIORITY

The present patent application is a division of U.S. application Ser. No. 18/455,382 filed on Aug. 24, 2023, which is a non-provisional of, and claims the benefit of, U.S. Provisional Pat. App. No. 63/453,020 filed on Mar. 17, 2023; the entire contents of which are incorporated herein by reference.

BACKGROUND

Vascular access to blood vessels is commonly used for percutaneous diagnostic and therapeutic procedures such as cardiac catheterization or peripheral vascular procedures. Vascular access may be obtained with a surgical cut down through the tissue to expose the vessel, or percutaneous access is more often obtained using procedures such as the Seldinger procedure where a needle is introduced into the vessel and followed by advancing a guidewire into the vessel. The guidewire can then serve as a rail over which other devices such as an introducer sheath can be advanced through the tissue into the vessel. The introducer sheath may be used to control hemostasis at the access point as well as facilitate introduction of a diagnostic or therapeutic catheter into the vasculature. Upon completion of the diagnostic or therapeutic procedure, the guidewire, sheath, and all other devices are removed from the patient. Pressure is applied to the vascular access site to ensure that bleeding is prevented. In some situations, the access site may not seal adequately resulting in unwanted and potentially dangerous blood loss. In some cases, one or more stitches may be applied to the vascular access site to close the puncture site, or plugs such as collagen plugs may be used to help close the puncture site. These devices or closure systems can have challenges associated with their use including adding additional procedure time, cost, and requiring additional training.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The attached figures include several drawings illustrating examples of a suture retention device.

DETAILED DESCRIPTION

Figure 1A:
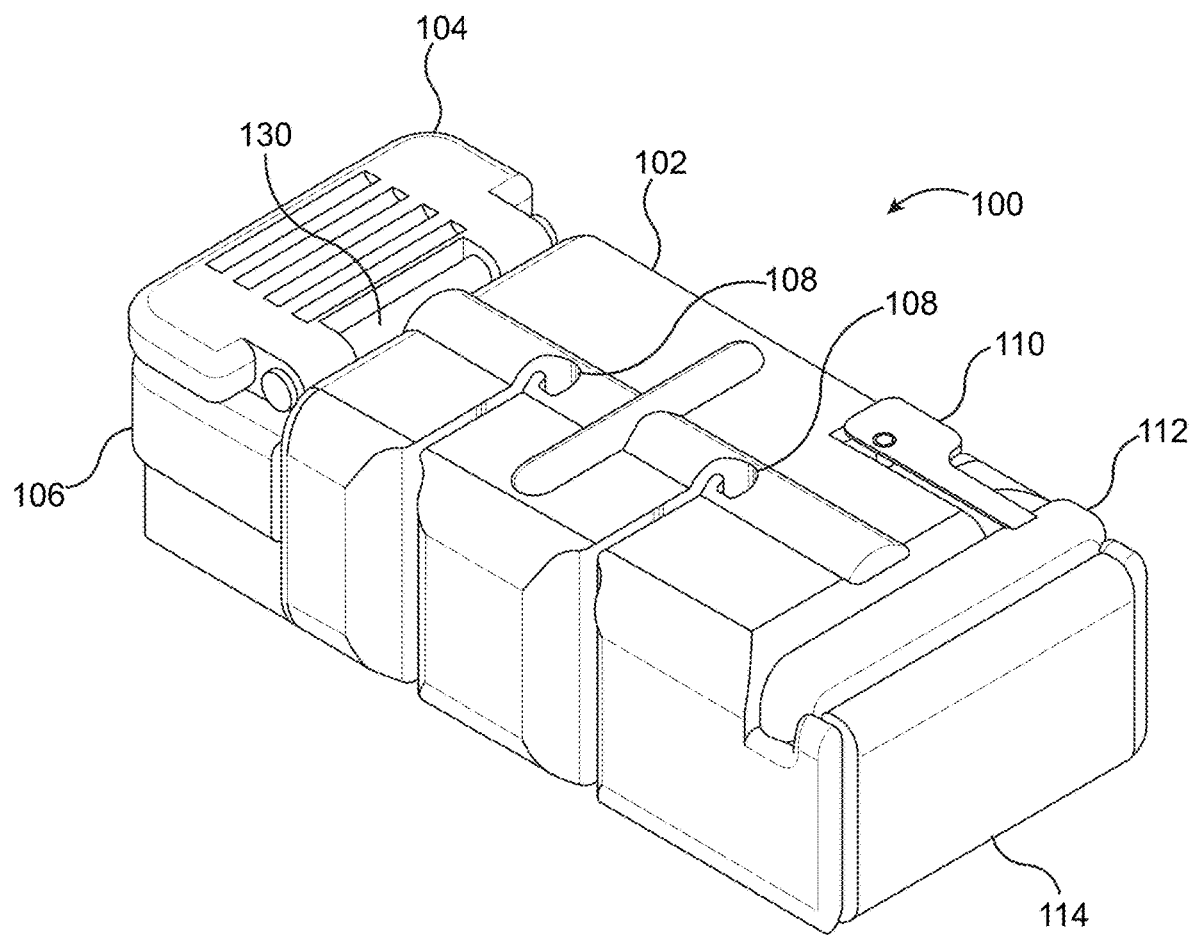
FIG. 1A illustrates a perspective view of an example of a suture retention device.

Vascular closure devices (VCDs) are medical devices used to achieve hemostasis of the small hole in the artery or vein after a cardiovascular procedure or endovascular procedure requiring catheterization. VCDs may be used on an artery or a vein, and this is not intended to be limiting.

Cardiovascular procedures requiring catheterization include diagnostic procedures that help diagnose diseased blood vessels or other tissue, and interventional procedures such as angioplasty, the placement of a stent and coronary thrombectomy which treat and repair diseased or damaged tissue. Other diagnostic and therapeutic procedures are also contemplated.

During such procedures, a small incision is made in the groin area and a hole is created in the femoral artery to gain access to the artery. This hole is referred to as the access site or puncture site. At the completion of the procedure, the hole needs to be closed. VCDs help achieve hemostasis and can be used in place of manual compression. VCDs may include collagen plugs, suture alone, or suture in combination with a suture retention device, or other devices used to help close the wound. Suture may be applied to the tissue adjacent the wound and then the suture may be tied off to maintain tension in the suture which helps close the wound, or a suture retention device may be used to help hold the suture in a desired position with a desired tension. In other procedures, access is obtained from a vein such as the femoral vein, such as in transseptal procedures where a catheter is advanced from the right side of the heart, across the septal wall into the left side of heart. In both situations, venous or arterial access, the puncture site must be closed to prevent unwanted bleeding. A vascular closure device may be used to facilitate closure of the puncture site. While the present disclosure will focus on suture retention devices, this is not intended to be limiting and one of skill in the art will appreciate that the examples disclosed herein may be used to hold or retain other filaments for medical or non-medical purposes. Therefore, the present disclosure is not limited to wound closure.

Examples of suture retention devices are disclosed herein. These examples are not intended to be limiting and are for illustrative purposes only.

Any of the devices disclosed herein may include a therapeutic agent that is carried on the device and delivered to the patient. For example, a local anesthetic like Lidocaine may be carried by any of the devices and delivered to the patient to alleviate pain. A clotting factor may be carried by the device to help ensure that the wound clots off and bleeding is avoided. The therapeutic agent may be an antibiotic to help prevent infections.

Any of the devices may include an adhesive backing to help temporarily attach the device to the patient's skin so that it does not fall off or hang loosely from the patient.

Any of the devices may include a foam backing that is disposed between the device and the patient to provide a cushion therebetween.

Any of the devices may be used to close any vessel in the body including arteries such as the femoral artery, iliac artery, radial artery, etc., or the devices may be used to close any of the veins in the body such as a femoral vein. Other non-medical uses are also disclosed herein.

Examples of Suture Retention Devices

Suture may be used to help close the puncture site and a suture retention device may be used to help keep tension on the suture so that the vascular access stays closed until hemostasis is achieved. As many of these patients can go home the day of the procedure, it may be desirable to have a feature in the device to make it easy for the patient to cut the sutures and remove the device at home, without having to return to the hospital or clinic. While these examples are described as venous closure devices, suture retention devices or vascular closure devices, one of skill in the art will appreciate that their use is not limited to veins only, and they may be used on arteries or other vessels and tissue. Any of the devices disclosed herein may be applied by a medical practitioner and removed by a medical practitioner or removed by a patient at home. Other uses including non-medical uses are also contemplated and disclosed herein.

Maintaining tension on the suture requires the suture to be captured either via friction force or through positive locking engagement if a knotless system is desired. Alternatively, a knot may be formed in the suture if desired.

In one example the interface between the suture and the body of the suture retention device is made via a plunger and a housing that receives the plunger. The portion of the plunger that interacts with the sutures can have varying geometries (rectangular, tapered, serrated etc.). The material of the interface between the plunger, suture and the body of the suture retention device can be made of varying degrees of hardness. Hard material would rely on the give in the suture material and flex in the suture retention device to accommodate sutures of varying diameters. Soft material would rely on the give in the material itself to accommodate sutures of varying thickness. The retention force of the suture needs to be optimized to minimize vessel or tissue injury while maximizing the amount of force it takes for the suture to slip.

The cross-section of the plunger can be rectangular, circular or any other shape to best fit the overall size of the suture retention device. In the images disclosed herein, rectangular and cylindrical plungers are illustrated but this is not intended to be limiting. The figures show the use of optional "O-rings" of material of different durometer to optimize the suture retention force.

In another example the "plunger" is spring loaded where, upon pressing the plunger downward into the housing opens up a channel to insert the sutures and upon releasing the plunger, the plunger is pushed back by the spring force and the channel space is diminished creating a hold on the sutures.

In another example the sutures are passed through the gap between the inner and outer components of the suture retention device. Then either the inner or outer body of the suture retention device is twisted which creates a positive lock on the sutures.

The plunger can have locking features to provide additional suture retention force and prevent the plunger from being pushed out. This feature would have release options to allow the health care provider to release the plunger if required.

The cutting mechanism on the suture retention device can use any number of examples, the cutter could be manually operated or spring operated. In the manually operated version the cutter holder would be pressed by the patient or the health care provider and this pushes a blade attached to the holder through the suture cutting it as near as possible to the skin. In the spring-loaded version removal of a brake or a dowel pin would release the cutter holder under tension from a spring and pull/push it towards the sutures and make the cut.

The interface of the suture retention device with the skin can be a soft foam or silicone substrate layer. The foam could be coated with antimicrobial, antibacterial analgesic and/or coagulant doped material to minimize chances of infection and help with pain relief, etc.

The foam could also be coated with the combination of the above therapeutic agents to get enhanced effect.

In another example, the cutter safety stop element is attached to an adhesive tape with a handle on one end such that when the tape is peeled off, the cutter safety stop is removed with the tape.

Figure 1B:
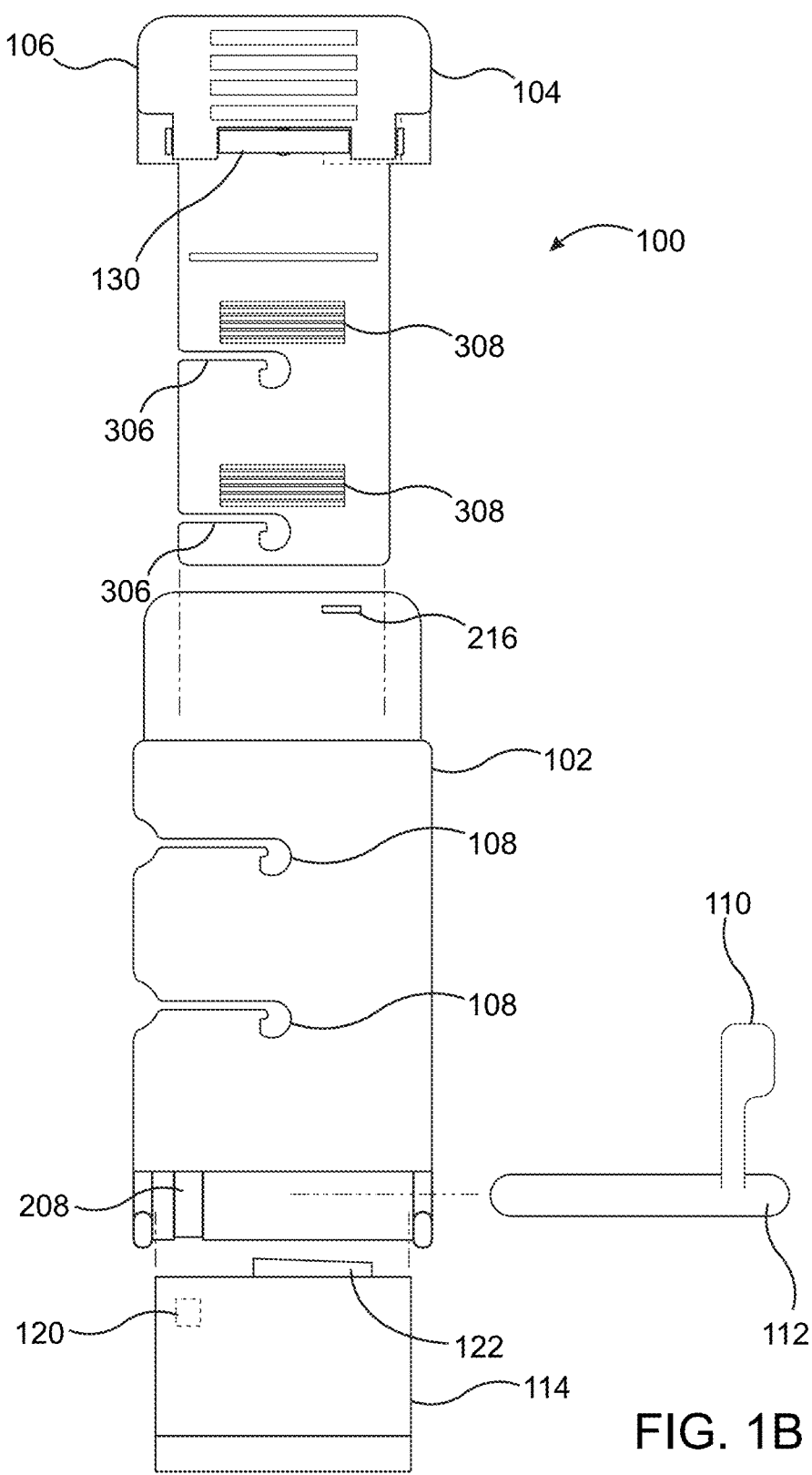
FIG. 1B shows an exploded top view of the device in FIG. 1A.
Figure 1C:
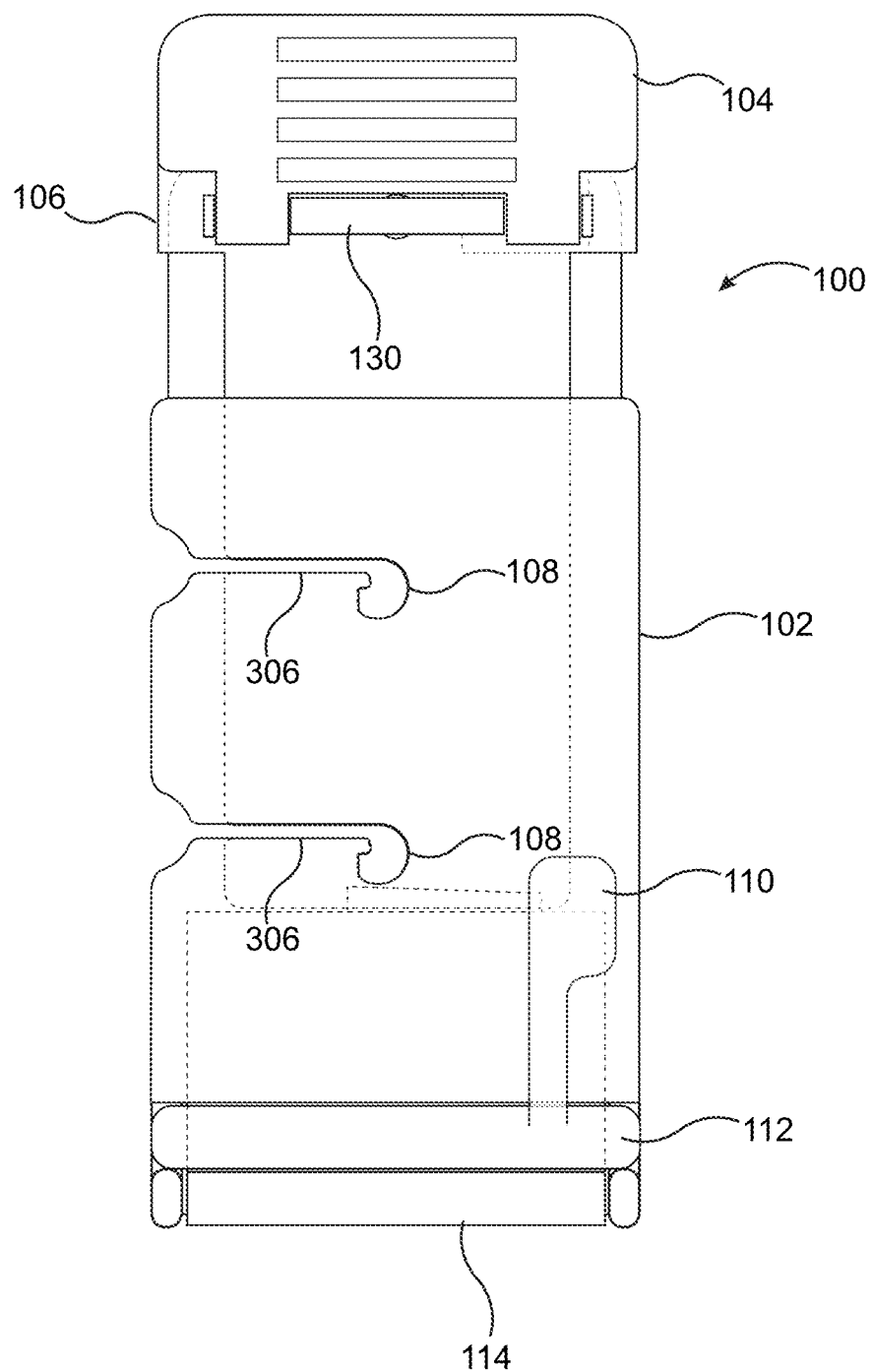
FIG. 1C shows a top view of the device in FIG. 1A.
Figure 1D:
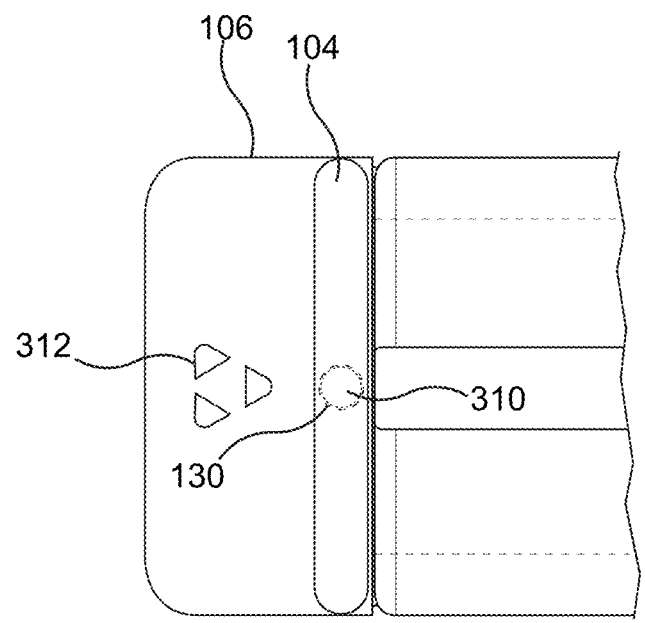
FIGS. 1D-1E show a top view of an example of actuation of the plunger release tab.
Figure 1E:
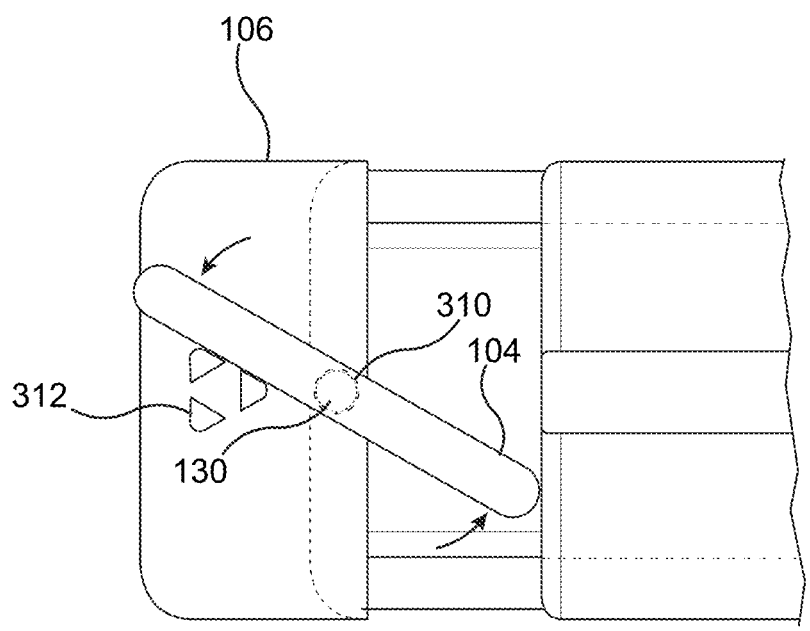

Turning now to FIGS. 1A-1E which show an example of a suture retention device 102. The suture retention device may be supplied alone or in combination with other components such as one or more suture filaments. FIG. 1A shows a perspective view of the device in the closed position and FIG. 1B shows an exploded view of the device from a top view. FIG. 1C shows a top view of the device in the open position. FIGS. 1D-1E show a top view of the actuation of a release tab to retract the plunger from a closed configuration to an open configuration.

In FIG. 1A, the suture retention device 100 includes a housing 102, a release tab 104, a plunger 106, one or more housing suture slots 108 (here there are two housing suture slots), a cutter release tab 110, a stop element 112, and a cutter element 114. The plunger also has one or more plunger suture slots but they are best seen FIG. 1B. The number of suture slots in the plunger may match the number of suture slots in the housing.

The housing 102 may be clear so that an operator may see into the housing and visualize the position of the plunger 106 in the housing or sutures (not shown in FIG. 1) disposed in the slots 108. To help visualize the plunger through a clear housing, the plunger may be colored, such as an off-white color or any other desired color. The plunger also has plunger suture slots but they are not visible in the view of FIGS. 1A-1E and will be illustrated below. The housing 106 includes a channel for slidably receiving the plunger 106, and also includes a channel for slidably receiving the cutter element 114. The stop element 112 is releasably coupled with the housing 102 once the release tab 110 is released from the housing. The release tab 110 may be an adhesive tape which is coupled to the housing 102 and the stop element 112, or a pin in a recess may be used as will be discussed below.

Another release tab 104 may be used to help remove the plunger from the housing, fully or partially. Release tab 104 maybe pivoted upward away from the upper surface of the plunger and then rotated along a central axis which may be orthogonal or transverse to the plane of the upper surface of the plunger. This actuation helps to retract the plunger out of the housing when it is desired to realign the suture slots in the plunger with the suture slots in the housing in order to allow repositioning of the suture in the housing suture slots 108. A pin 130 may be used to couple the release tab 104 to the plunger. The pin may be T-shaped to allow rotation along two axes as will be discussed and illustrated further below.

FIG. 1B shows a top surface of the suture retention device in an exploded view and allows additional features of the device to be observed that are not always visible in FIG. 1A. For example, the housing 102 may include protrusion 216 which may be received in a recessed region of the bottom of the plunger to prevent the plunger from falling out of the housing and decoupling. The opposite end of the housing also includes a recessed region 208 which may be used to receive a protrusion 120 on the bottom of the cutter element 114 to keep the cutter element from falling out of the housing and decoupling. The cutter element 114 includes a blade with a sharpened cutting edge 122 that can cut a suture filament. The cutting edge may be angled so that when the blade is pushed against a suture filament, the blade provides a shear cutting action against the suture filament to more cleanly and easily cut the filament than if the cutting blade is pushed straight into the filament. These features are described below in more detail. The plunger 106 is also shaped to have an elongate narrow body and an enlarged head region to form a T-shaped plunger as further described below in FIG. 3. The plunger optionally includes surface features or texturing 308 which may help create a greater interference fit between the plunger and the inner surface of the housing when the device is in the closed position. Here, the surface features include a plurality of rows of raised surfaces forming peaks and valleys. The plunger also has one or more plunger suture slots 306 which cooperate with the housing suture slots to receive the suture filament when the device is in the open position and to hold the suture filament when the device is in the closed position. These features are described in more detail later in this specification. Other aspects of FIG. 1B are the same as FIGS. 1A and 1C.

FIG. 1C shows the device of FIGS. 1A-1B in the open configuration. Here, the housing suture slots 108 are aligned with the plunger suture slots 308 to provide a pathway that is open from the bottom of the housing, through the plunger and to the top of the housing that is able to receive a suture filament. Therefore, in the open configuration, the J-shaped slots are aligned. Also, the release tab 104 is shown in the collapsed configuration where it lies flat against the plunger when not in use. The release tab 104 may be rotated up vertically so that it may be grasped by an operator, such as by the thumb and forefinger and then rotated clockwise or counterclockwise to the retract the plunger out of the housing if needed. Other aspects of FIG. 1C are the same as in FIGS. 1A-1B.

FIGS. 1D-1E show actuation of the release tab 104. In FIGS. 1A-1C, the release tab 104 in in the closed configuration, where the release tab lays flat against the plunger. The release tab is therefore flat and disposed in a plane parallel with the top surface of the plunger 106. When an operator wishes to remove the plunger from the housing, the operator may grasp the enlarged head portion of the plunger and pull the plunger out of the housing. However, in some situations, the enlarged head may not provide enough purchase to pull the plunger. Therefore, the release tab may be used to facilitate release of the plunger from the housing. In order to use the release tab, the user will rotate or flip the release tab upward from its horizontal position so that it is in a vertical position. Here, the release tab is now disposed in a plane that is transverse to the top surface of the plunger or orthogonal thereto, and the release tab may be protruding outward and away from the top surface of the plunger as seen in FIG. 1D. This now provides adequate purchase for the user to grasp. The release tab pivots upward around a T-shaped pin 130 which is inserted into an aperture 310 in the plunger that allows rotation or pivoting along the horizontal or upper bar portion of the T-shaped pin, and also allows rotation along the long stalk or vertical portion of the T-shaped pin. Further details about the T-shaped pin are described below. Once the pin is in the vertical position, the user may then rotate the release tab about the vertical axis of the vertical portion of the T-shaped pin. Rotation along the vertical axis presses one end of the release tab against the housing while the opposite end of the release tab moves away from the housing. This moves the plunger outward and away from the housing. Protrusions 312 prevent over rotation of the release tab such that when the release tab abuts the protrusions 312, further rotation is prevented. Here, three protrusions are shown, but any number of protrusions such as one, or two, or three, or more protrusions may be used as the stop. FIG. 1E shows the rotation of the tab to release the plunger from the housing.

Figure 2A:
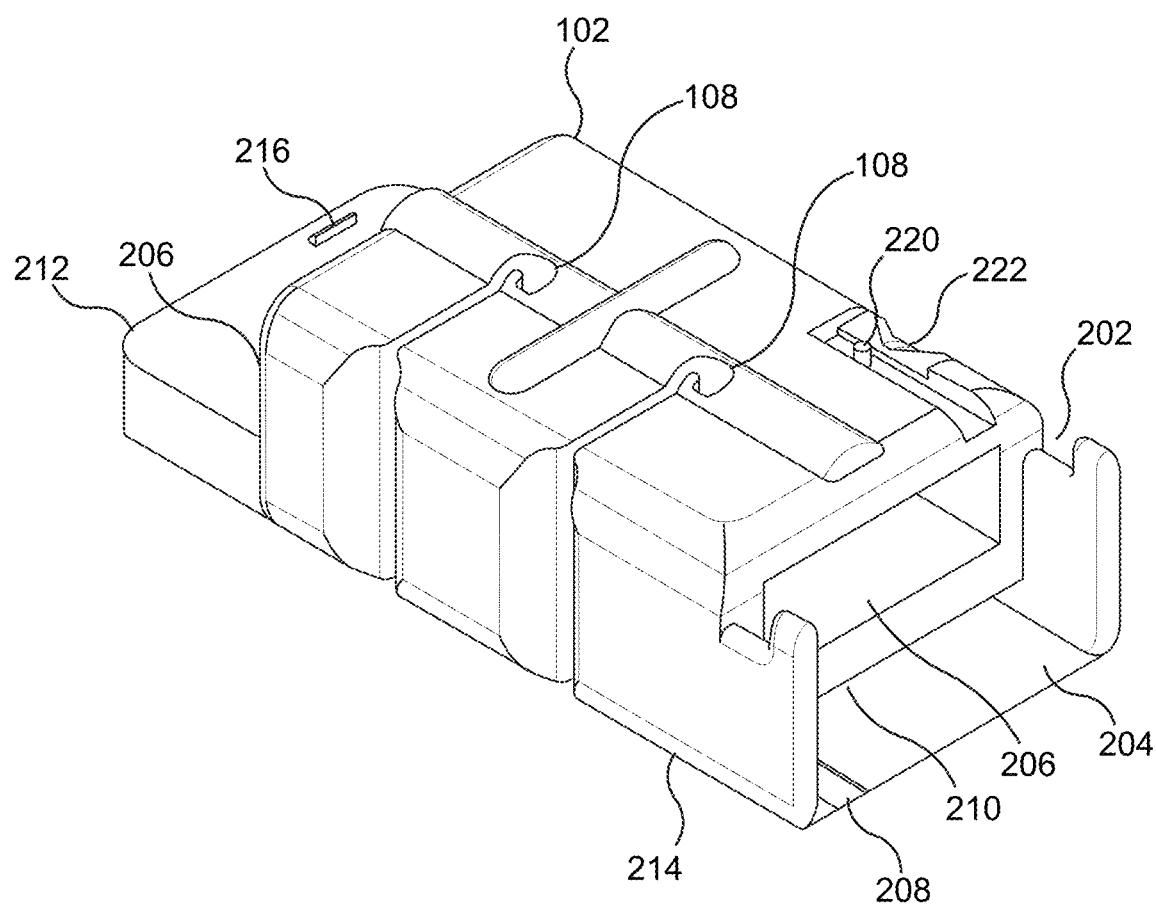
FIG. 2A shows a perspective view of the housing in FIG. 1A.

FIG. 2A shows the housing 102 with all the components removed, such as the plunger 106, stop element 112, and cutter element 114 removed. Also, the release tabs 104, 110 are also removed. Therefore, only the housing 102 is seen in FIG. 2A. Here, a flat planar surface 212 extends from one end of the housing and a channel 206 is disposed in the housing and extends along the longitudinal axis toward the opposite end of the housing. In this view, the channel is shown on the right side of the housing but is not visible on the left side of the housing. The channel may extend all the way from left to right side, or the channel may extend from the left side toward the right side of the housing, but the channel may not be a through channel all the way through the right side of the housing. The flat planar surface 212 provides a surface for supporting the plunger when the plunger is inserted into the channel 206. Additionally, the flat planar surface 212 may include a protrusion 216 which is received in a cooperating recess in the bottom of the plunger. The protrusion prevents the plunger from falling out of the channel 206 when the plunger is inserted in the channel. In other examples, the protrusion and the recess may be switched with one another so that the protrusion is on the plunger and the recess is in the housing. Also, one side of the protrusion may have an angled surface that facilitates insertion of the plunger into the channel while the opposite side of the protrusion may be a straight vertical portion that prevents the protrusion from easily falling out of the recess.

The housing may be clear so that the user can visualize the position of the plunger in the housing and also the clear housing allows the user to see the suture filaments when they are disposed in the slots 108. Here, the housing has two housing suture slots 108. Each slot is transverse to the longitudinal axis of the housing and may be orthogonal to the longitudinal axis of the housing. The slots may have a long linear portion and a curved and enlarged head region that forms a J-shaped slot for receiving the suture filament.

The enlarged head region helps to hold the suture filament and also helps keep the suture filament from falling out of the slot.

The opposite end of the housing 102 (the right side in FIG. 2A) shows the channel 206 for the plunger extending through the housing wall, but as described above, the channel 206 does not have to extend through the wall of the housing and the channel may be a blind channel.

A cutter channel 210 may be disposed in the housing and the cutter channel may extend along the longitudinal axis of the housing. The cutter channel is open on the right side of the housing and may extend all the way through the housing through the wall on the left side of the housing, or it may be a blind channel that does not extend through the wall of the housing on the left side. The cutter channel 210 is disposed under the plunger channel 206. A bottom surface 204 of the housing 102 may include a recessed region 208 that can receive a protrusion on the bottom of the cutter element (not seen in this view). When the protrusion is received in the recessed region, this prevents the cutter from falling out of the cutter slot and decoupling from the housing. In other examples, the protrusion on the cutter element and the recess in the housing may be reversed so that the protrusion is on the housing and the recess is on the cutter element.

The right side of the housing also includes a pair of walls 202 with a higher region and a shorter region that forms a shoulder region that can support a stop element (not seen in this view). The stop element prevents movement of the cutter element through the cutter channel and therefore prevents inadvertent severing of the suture filaments. The stop element is easily removed from the shoulder region which then allows the cutter element to be advanced into the cutter channel to sever one or more of the suture filaments. The stop release tab 110 (seen in FIG. 1) may be used to help keep the stop element in place and when the stop release tab is removed, the stop element can be actuated or is also easily removed.

A protrusion such as a pin 220 may extend upward and out of the top surface of the housing 102. The pin may be received by an aperture 710 in the cutter release tab 110 (best seen in FIG. 7). This helps keep the cutter release tab from unwanted movement and therefore helps keep the stop element 702 in its position where it prevents unwanted movement of the cutter blade. In other examples, the position of the protrusion and the aperture may be exchanged with one another. In other examples, the cutter release tab may also have adhesive on a bottom surface to help it stick to the housing to prevent movement. The adhesive may be used alone or in conjunction with the protrusion and aperture features.

A recessed concave region 222 on the upper surface of the housing 102 allows a user to insert a finger or other object under the cutter release tab and lift the tab to disengage it from the protrusion, thereby allowing the user to remove the stop element so that the cutter may be actuated to cut a suture filament.

A bottom surface 214 of the housing may be flat and planar so that it rests flush against a patient's body in use. Additionally, a substrate may be applied to the bottom surface. The substrate may be a foam material to prevent excessive pressure being applied to the patient, or the substrate may carry a therapeutic agent that is eluted therefrom, such as a pain reliever such as Lidocaine, or an antibiotic that helps prevent infection. Other therapeutic agents may also be used.

Figure 2B:
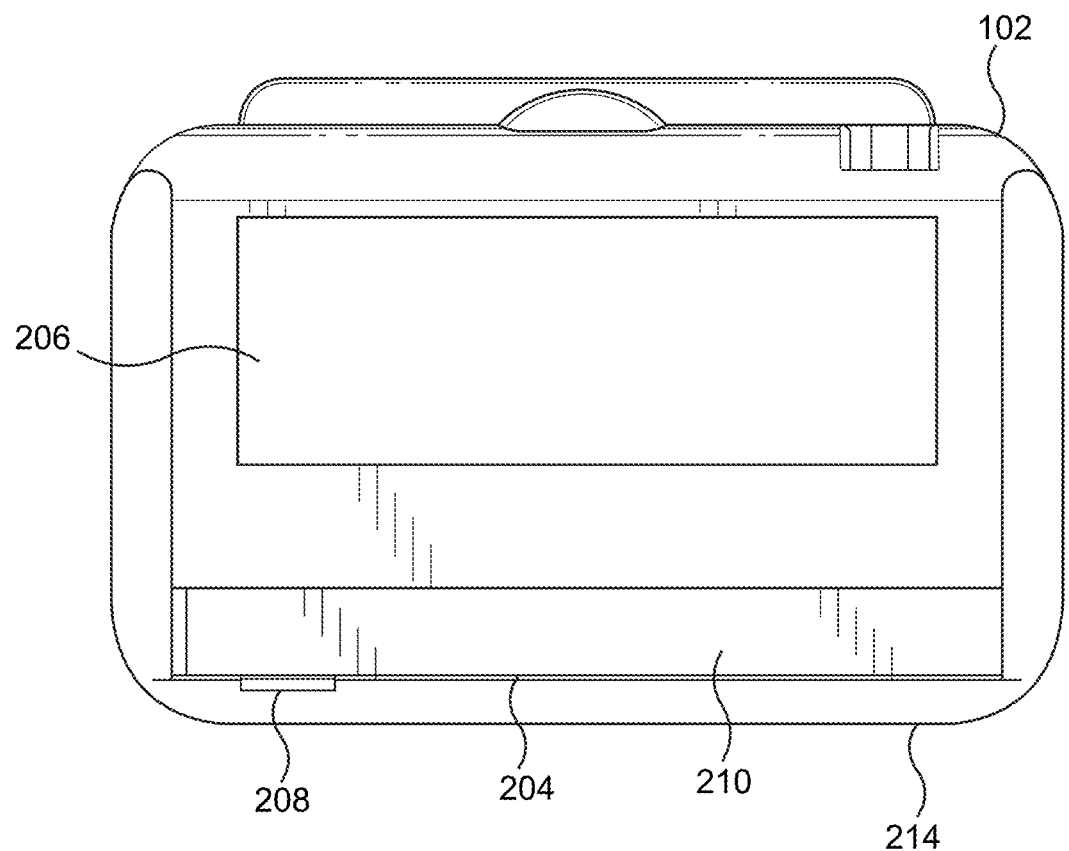
FIG. 2B shows an end view of the housing in FIG. 2A.

FIG. 2B shows an end view of the housing in FIG. 2A. This view illustrates the right end of the device in FIG. 2A which is the end with the cutter element. FIG. 2B highlights the plunger channel 206 which as previously described above may extend all the way through the housing or may be a blind channel that is only open on the left side of the housing and does not pass through housing wall on the right side of the housing. The cutter channel 210 is also visible in this view and is a channel that is open on the right side of the housing and extends through the housing at least up to the housing suture slots so that the blade may be pushed inward enough to cut the suture filament. The cutter channel may extend all the way to the left side of the housing, or it may be a blind channel that only extends partially through the housing and does not exit the left side of the housing. Other aspects of the housing are the same as previously described above in FIG. 2A.

Figure 2C:
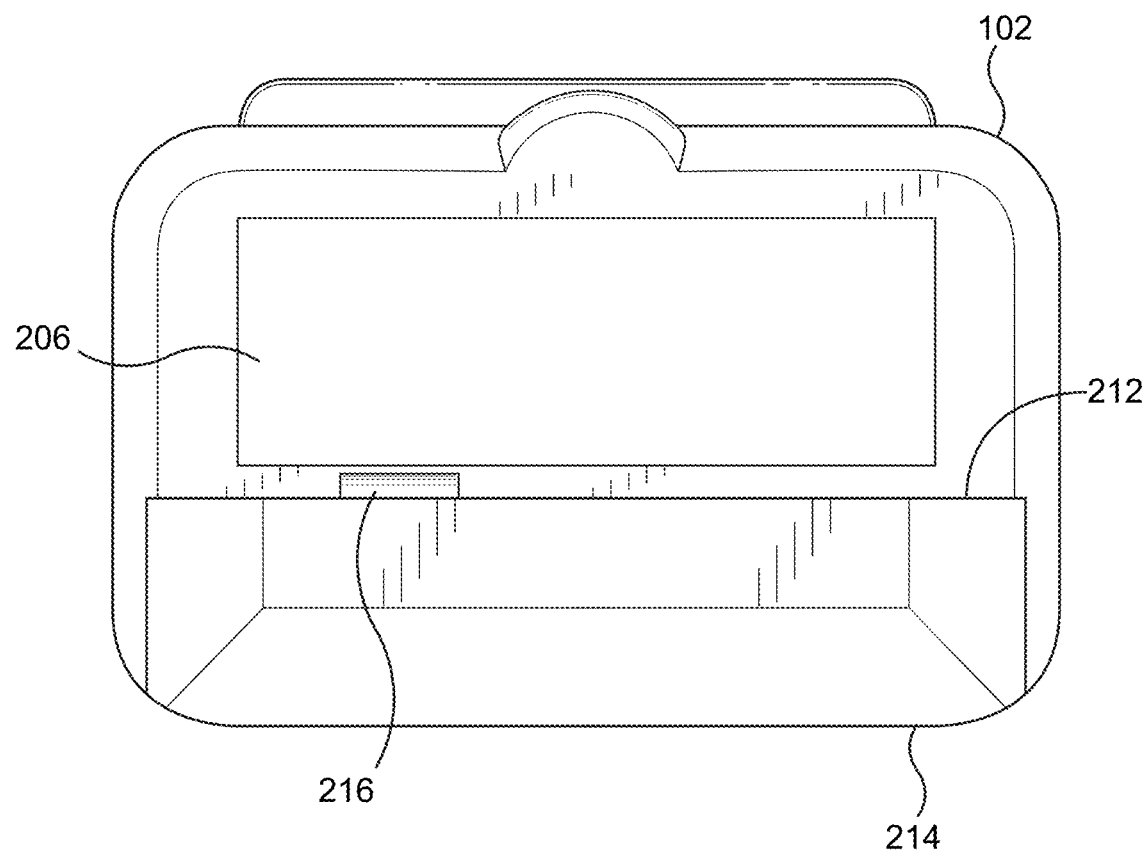
FIG. 2C shows an end view of the opposite end of the housing in FIG. 2A relative to FIG. 2B.

FIG. 2C is also an end view of the housing in FIG. 2A. This view illustrates the left end of the device in FIG. 2A, which is the end with the plunger. FIG. 2C highlights the plunger channel 206 which exits the housing on this end so that it can receive the plunger. Other aspects of the housing are the same as previously described above in FIG. 2A and FIG. 2B.

Figure 3:
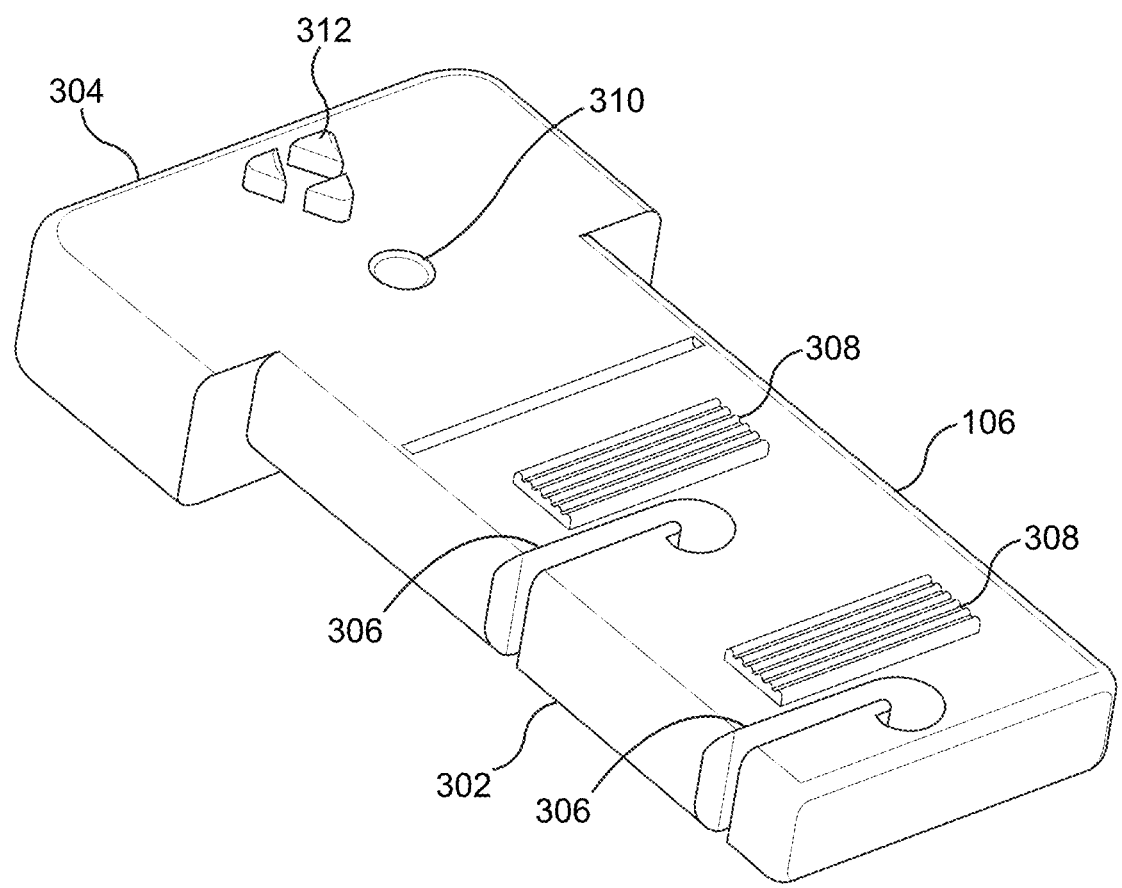
FIG. 3 shows a perspective view of an example of a plunger highlighting a top surface.

FIG. 3 shows the plunger 106 removed from the housing. Here, the plunger includes an elongate narrow region 302 and a wider enlarged head region 304 that forms a substantially T-shaped plunger. The narrow region 302 is received in the plunger channel in the housing, and the enlarged head region is used to push the plunger into the channel, and also used to remove the plunger from the channel.

The plunger also includes a plunger suture slot 306. Here there are two such slots but there may be more or fewer slots as required. The plunger suture slot includes an elongate linear portion that is transverse to the longitudinal axis of the plunger and may be orthogonal. The plunger slot also includes an enlarged head region that is coupled to the elongate slot to form a J-shaped slot. The enlarged head helps hold the suture filament so that the suture filament is retained in the plunger slots and does not fall out. When the plunger is inserted into the channel in the housing, the plunger has an open position and a closed position. In the open position, the plunger suture slots 306 are aligned with and cooperate with the housing suture slots so that the suture filament may be easily inserted or removed from the slots. The plunger in this configuration is partially disposed in the channel in the housing, but not all the way. In the closed configuration, the plunger suture slots are axially offset from one another and therefore misaligned with the housing suture slots which results in an interference fit between the surface of the plunger, the inside wall of the housing and the suture filament, thereby preventing movement of the suture filament. In this configuration, the plunger is advanced further into the channel in the housing so that the slots are misaligned with one another.

Optionally texturing on the surface (on top, or on the bottom surface, or on both top and bottom surfaces) of the plunger may further enhance and create the interference fit between the plunger, housing and suture filament to help hold the suture filament and prevent movement. Here, the surface texturing is shown as a plurality of ribs protruding outward from the surface of the plunger and extending transverse or orthogonal to the longitudinal axis of the plunger.

The plunger 106 also includes an aperture 310 for receiving a pin coupled to the release tab 104 (seen in FIG. 1). This pin allows the release tab to rotate around the one or two or more axes of the pin depending on the pin being used, which may be orthogonal to the flat planar surface of the plunger in this example, on a top surface of the plunger. One or more protrusions 312, here, three protrusions may also be included on the enlarged head portion of the plunger and these protrusions may be used to limit rotation or prevent over rotation of the release tab when pivoting around the axis of aperture 310.

Figure 4:
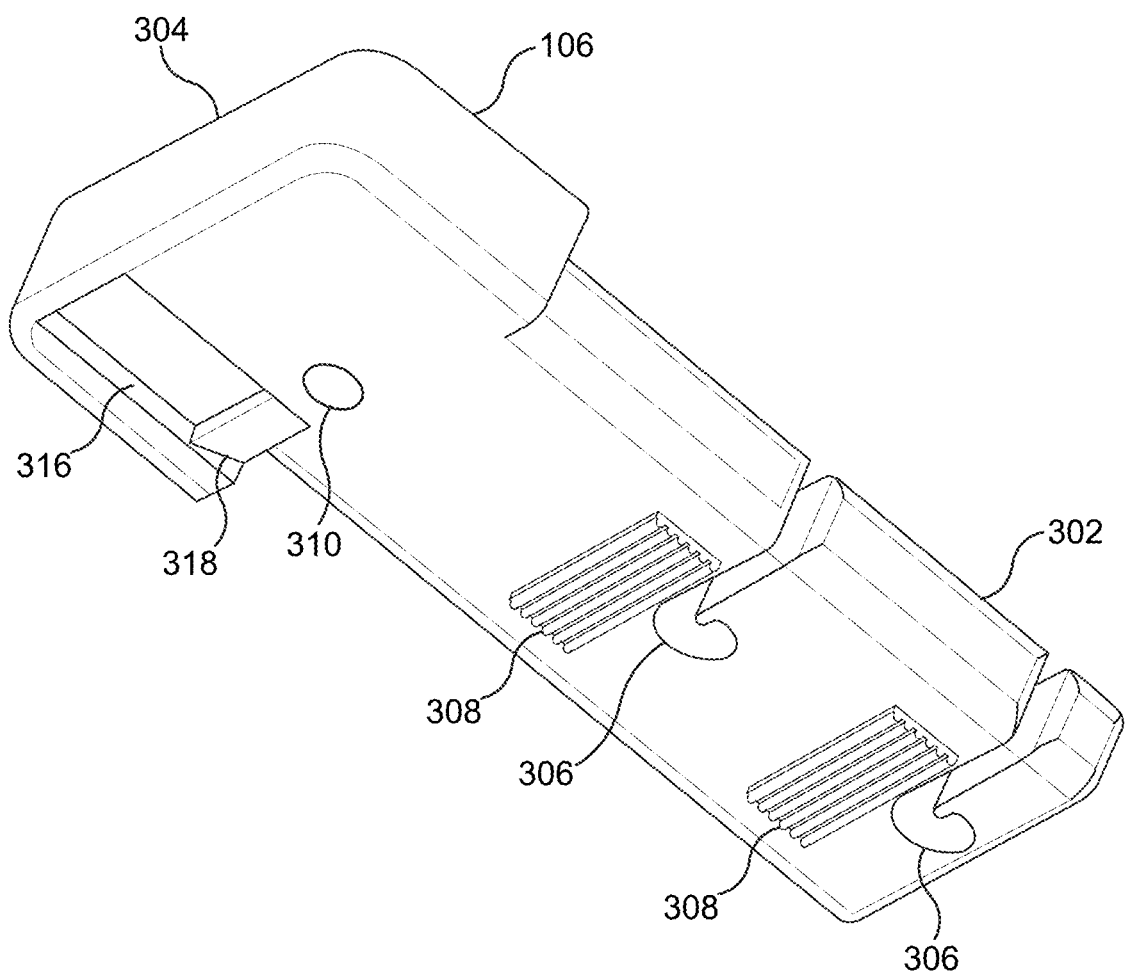
FIG. 4 shows a perspective view of a bottom surface of the plunger in FIG. 3.

FIG. 4 shows a bottom view of plunger 106. The bottom of the plunger may include a recessed region 316 which receives protrusion 216 on the housing. Once the protrusion is received in the recess, this prevents the plunger from falling out of the channel in the housing and the two components decoupling from one another. As mentioned above, the protrusion and the recess may be exchanged with one another so that the protrusion is on the plunger and the recess is on the housing. The recess 316 in this figure may also have an angled or ramped portion which helps the protrusion on the housing slide into the recess but helps to prevent the protrusion from moving out of the recess. The low end of the ramp may be closest to the narrow portion of the plunger, and the high end of the ramp may be closed to the enlarged head region of the plunger. Other aspects of the bottom surface of the plunger are generally the same as the top surface and therefore like numbers indicate like features for the top and bottom surfaces, and the detailed description will not be repeated for the sake of brevity.

Figure 5A:
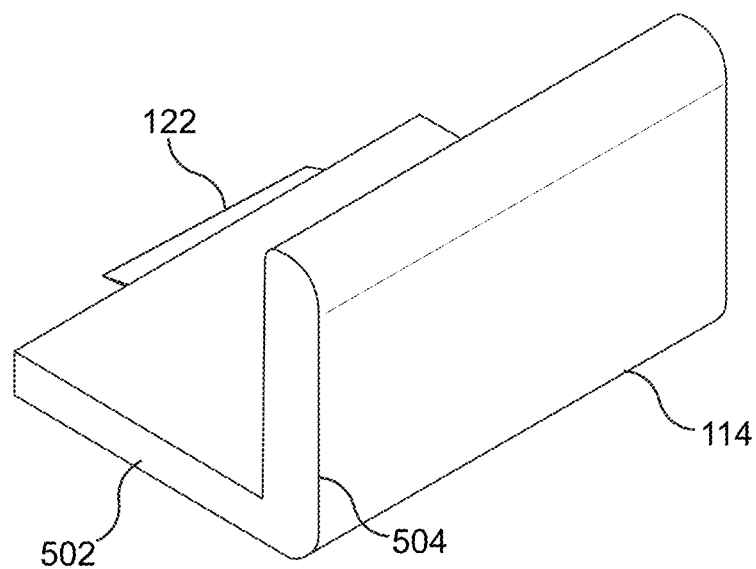
FIGS. 5A-5B show perspective views of an example of a cutter element.
Figure 5B:
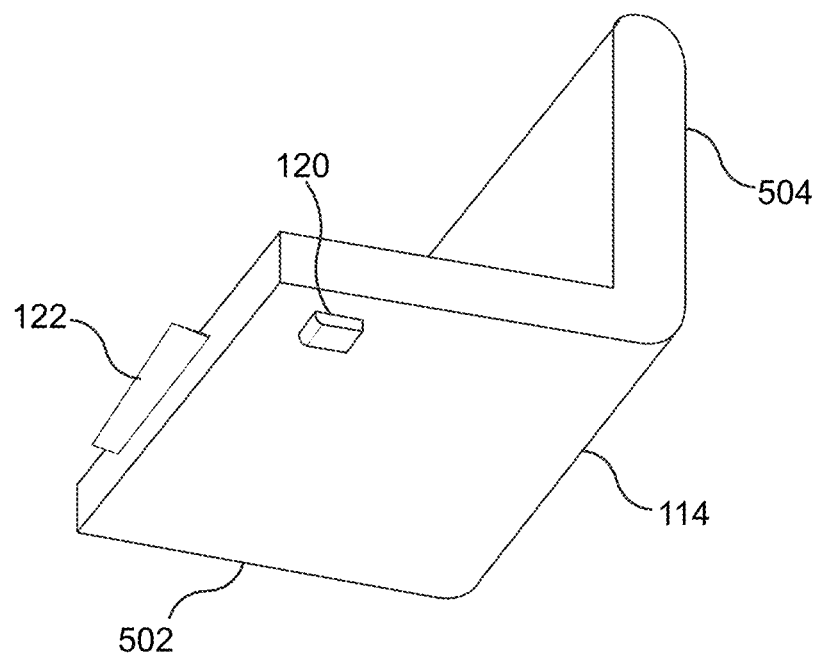

FIGS. 5A-5B show the upper and lower sides of the cutter element 114. The cutter element 114 is an L-shaped piece with a vertical wall 504 and a horizontal wall 502 that are coupled together to form the L-shaped component. The lower wall 502 is a flat planar section that slides in and out of a channel in the housing. The leading end of the lower wall 502 is the portion of the lower wall that first enters the cutter channel in the housing also includes a blade 122 with a sharpened cutting edge that can cut through suture filaments. The cutting edge may be straight and parallel with the leading edge of the lower wall, or as seen in FIG. 5A, the cutting edge is angled relative to the leading edge of the cutter element which provides a shearing cutting action as the cutting element is advanced into the cutter channel and pushed against the suture filament. The vertical wall 504 is transverse to the lower wall which may be in a horizontal plane while the vertical wall lies in a vertical plane which may be transverse or orthogonal to the lower wall. The top of the vertical wall may be rounded to remove sharp edges which could damage or cut a surgeon's gloves in use.

FIG. 5B shows the lower surface of the cutter element 114 and more clearly shows the cutting element 122 and also illustrates the protrusion on the cutter element which is received in a recess in the housing to keep the cutter element from falling out of the cutter channel in the housing. Other aspects of FIG. 5B are generally the same as in FIG. 5A.

Figure 6A:
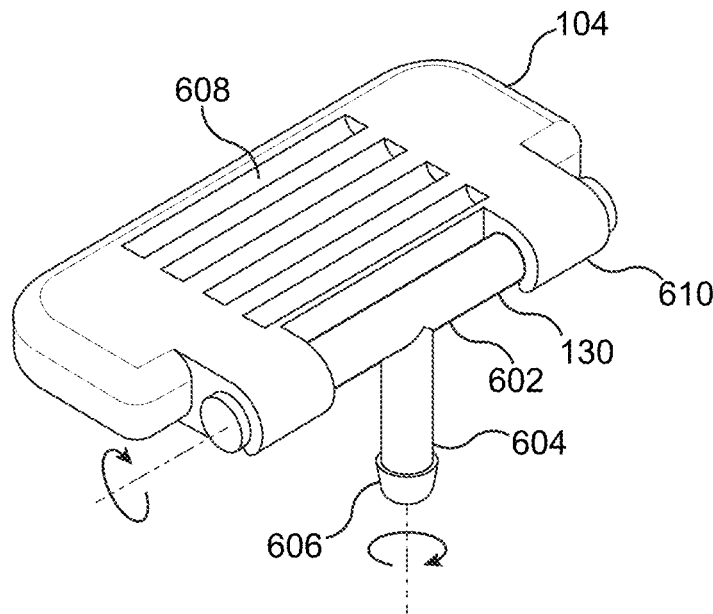
FIGS. 6A-6C show perspective views of an example of actuation of a release tab.
Figure 6B:
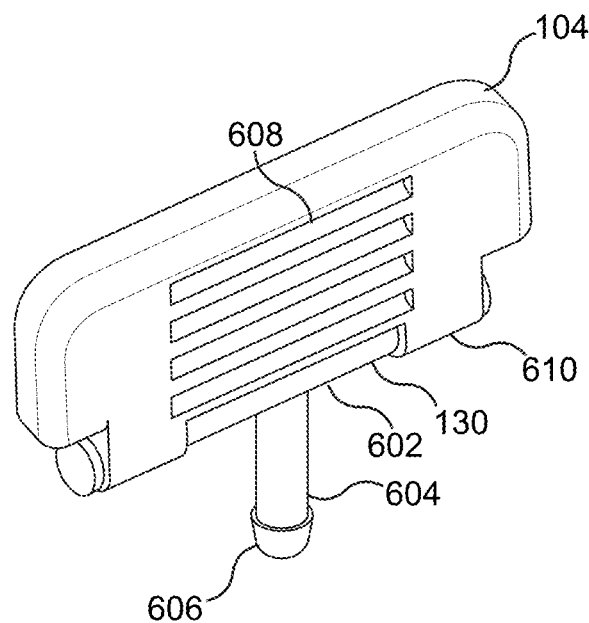
Figure 6C:
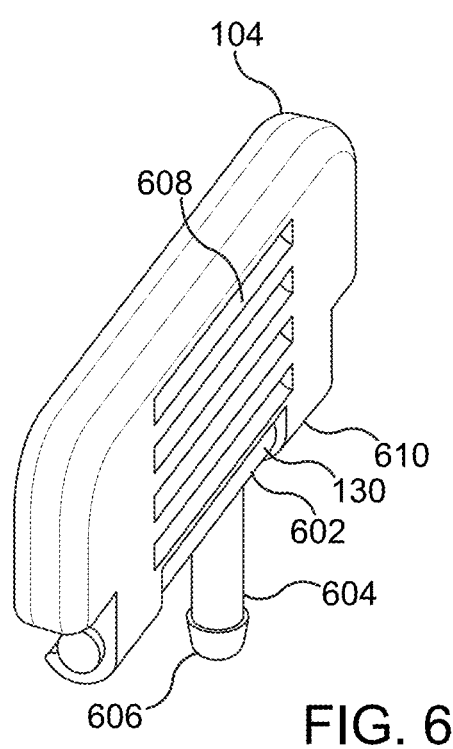

FIGS. 6A-6C show the release tab 104 and the pin 130 which couples the release tab to the plunger. The pin 130 is a T-shaped pin with a horizontal portion 602 and a vertical portion 604 that allows the tab to rotate in two directions.

FIG. 6A shows the rectangular shaped release tab 104 which may also be any other desired shape with a flat surface and optional texturing 608 which may facilitate the operator to grasp the release tab. In this configuration, the release tab lays flat and horizontally when it is not being used and the release tab will lay flat against a surface of the plunger. The horizontal portion 602 of the pin 130 has a pin with enlarged ends, and either end of the pin is coupled to wings 610 on either side of the release tab thereby allowing rotation around the longitudinal axis of the horizontal portion of the pin. Coupling may be with a snap fit or other techniques known in the art. The vertical portion of the pin 604 is coupled to the horizontal portion of the pin and allows rotation around the longitudinal axis of the vertical portion of the pin. Therefore, the pin can move along two axes. The two axes are transverse to one another and may be orthogonal to one another. A barb 606 on the vertical portion of the pin may be used to help ensure a tight press fit with the receiving aperture 310 seen in the plunger illustrations.

In FIG. 6B, the release tab has been rotated upward and away from its flat position and now stands vertically upward. It may be rotated to any angle between 0 degrees (tab is flat) to 90 degrees (tab is vertical and orthogonal to the plunger). The release tab may be further rotated past 90 degrees so that the tab starts to lay flat again on a side of the plunger opposite the original tab position. Therefore, the tab may be rotated greater than 90 degrees to any position up to 180 degrees (tab now flat again). When the tab is rotated up from the flat position (0 degrees or 180 degrees), it provides a surface that can easily be grasped by the user and then rotated.

FIG. 6C shows rotation about the longitudinal axis of the vertical portion of the T-shaped pin. In this situation, one end of the release tab approaches a wall of the housing while the opposite end of the release tab moves away from the plunger wall and toward the protrusions in the plunger (best seen in FIG. 1E). When the end of the release tab presses against the housing wall, the plunger is forced outward and away from the housing moving the plunger out of the channel in the housing. The position of the plunger may be adjusted as desired, such as to a position where the suture slots on the plunger align with the suture slots on the housing to release the suture and allow the suture to move. Over-rotation of the release tab is prevented by the protrusions 312 on the plunger.

When actuation of the release tab and plunger are completed, the release tab may be realigned and placed back in the flat configuration so that it lays flat against the plunger.

Figure 6D:
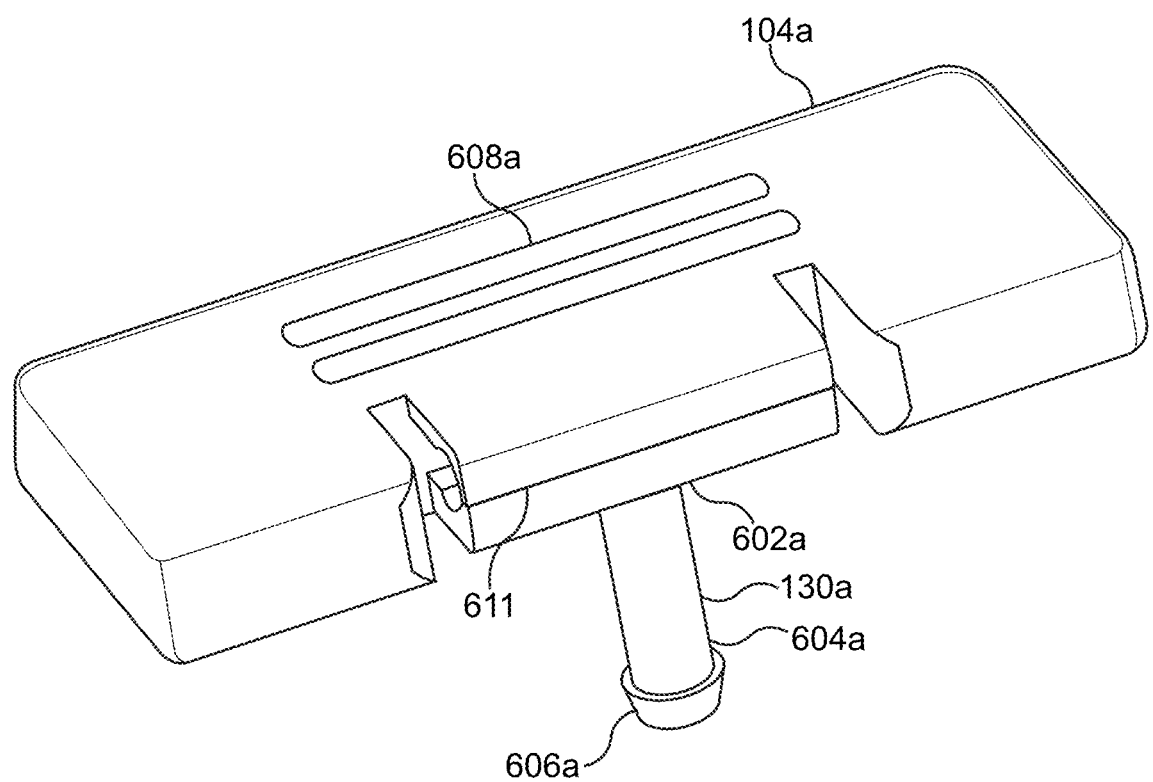
FIGS. 6D-6F show perspective views of another example of actuation of a release tab.
Figure 6E:
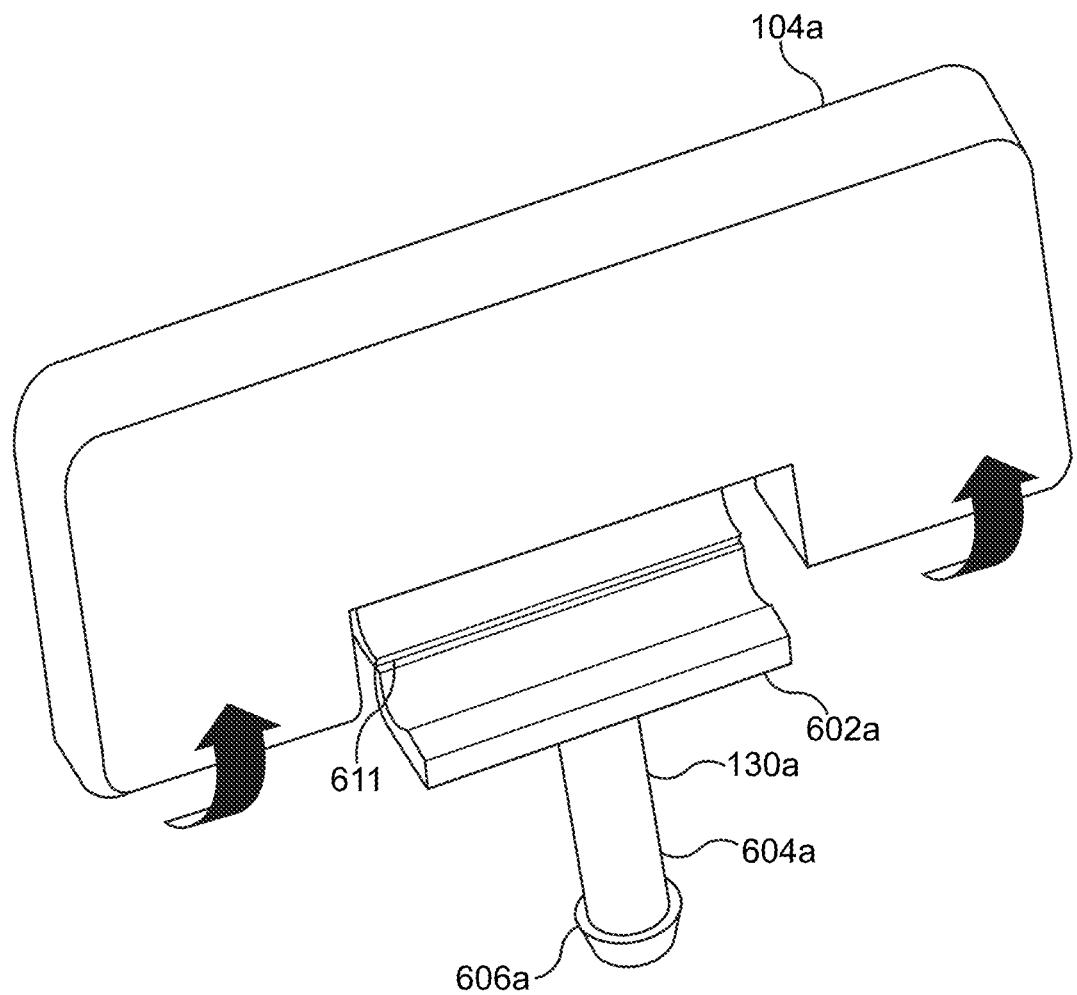
Figure 6F:
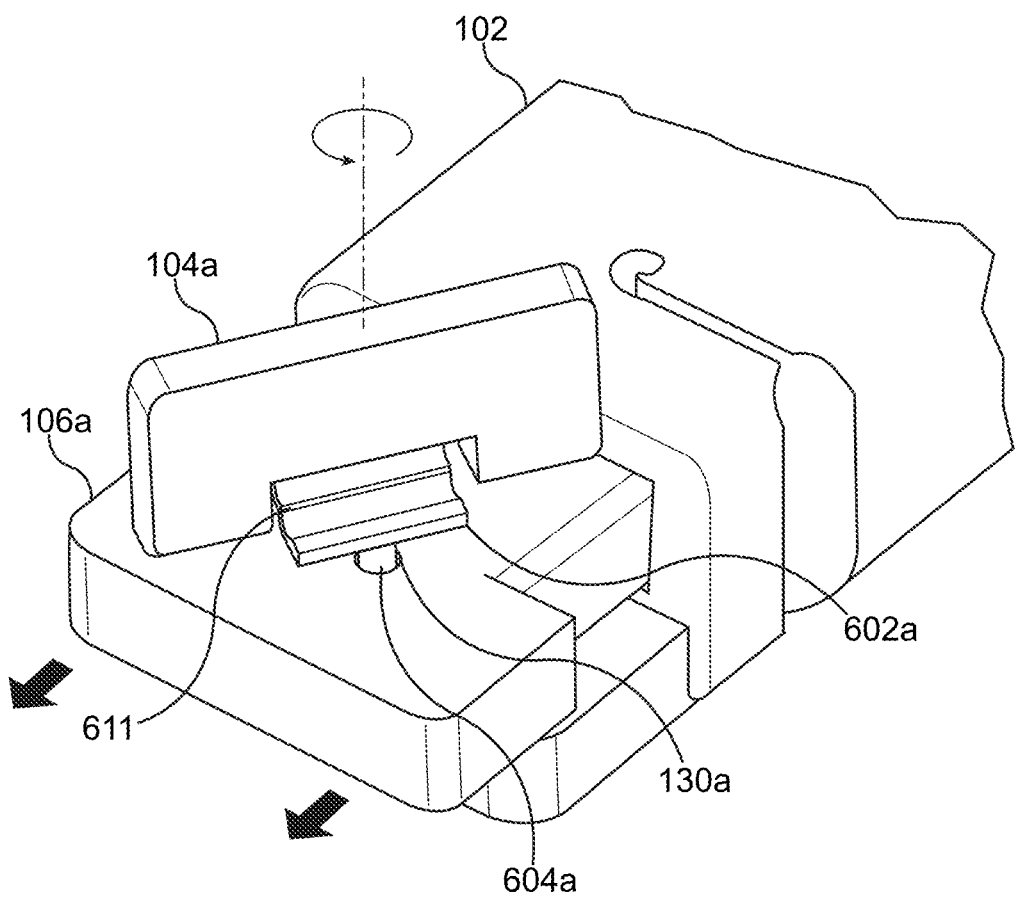

FIGS. 6D-6F show actuation of another example of a release tab 104a to retract the plunger from the housing. The release tab 104a includes a pin 130a that is similar to the pin 130 previously described above. The pin 130a in this example is a cylindrically shaped pin that has a vertically oriented portion 604a when coupled with the plunger and a barbed shaped end 606a that allows rotation about the longitudinal axis of the pin 130a. This pin 130a does not have the horizontal portion that the previous example did. The pin 130a couples the release tab 104a to the plunger. The release tab 104a includes a living hinge 611 which is disposed between the release tab 104a and the pin 130a. The living hinge 611 allows the release tab 104a to pivot from a flattened closed position to an open vertically oriented position that can be easily grasped by an operator. In the closed position, the release tab is generally in a flat planar configuration that is substantially parallel with an upper surface of the plunger and the release tab lays substantially flat against the plunger. In the open position, the tab may be rotated or pivoted upward and away from the flat position to a vertical position that may be transverse or orthogonal to the flat position. Thus, the tab may rotate from 0 degrees up to 90 degrees and any position in between where 0 degrees represents the release tab laying flat against a top surface of the plunger and 90 degrees represents the release tab extending vertically and orthogonally relative to the top surface of the plunger. Additionally, the release tab may also be further rotated past the 90 degree vertical position back toward a flattened position away from the original flattened position, and therefore the tab may be rotated to any position from 90 degrees to 180 degrees if desired, where 180 degrees represents the release tab laying flat against the plunger top surface.

FIG. 6D shows the rectangular shaped release tab 104a which may also be any other desired shape with a flat surface and optional texturing 608a which may facilitate the operator to grasp the release tab 104a. In this configuration, the release tab lays flat and horizontally when it is not being used and the release tab will lay flat against a surface of the plunger. Here, the living hinge 611 is in a closed position. The living hinge may be a thin resilient piece of material such as a polymer that couples the release tab to another portion 602a of the release tab that is coupled to the pin 130a. The thin resilient material can bend from the open position to the closed position and back, many times without breaking caused by fatigue thereby forming the living hinge 611. The vertical portion 604a of the pin 130a is coupled to a bottom portion 602a of the release tab 104a and the living hinge 611 allows rotation or pivoting of the release tab along the longitudinal axis of the living hinge. Therefore, rotation of the release tab occurs along two axes, the first being rotation around the living hinge longitudinal axis, and the second being rotation around the longitudinal axis of the pin. The two axes are transverse to one another and may be orthogonal to one another. A barb 606a on the vertical portion of the pin may be used to help ensure a tight press fit with the receiving aperture seen in the plunger illustrations described herein.

In FIG. 6E, the release tab 104a has been lifted and rotated from the closed position in FIG. 6D to the open position. Here, the living hinge 611 is seen in the open position. The release tab has been rotated along the longitudinal axis of the living hinge as seen by the arrows, and has been rotated upward and away from its flat position and now stands vertically upward. It may be rotated to any angle between 0 degrees (where the release tab is flat) to 90 degrees (where the release tab is vertical and orthogonal to the plunger). The release tab may be further rotated past 90 degrees so that the tab starts to lay flat again on a side of the plunger opposite the original tab position. Therefore, the tab may be rotated greater than 90 degrees to any position up to 180 degrees (tab now flat again). When the tab is rotated up from the flat position (0 degrees or 180 degrees), it provides a surface that can easily be grasped by the user and then rotated about the longitudinal axis of the pin.

FIG. 6F shows rotation of the release tab 104a about the longitudinal axis of the vertical portion 604a of the pin 130a as indicated by the circular arrow. Here, the release tab 104a is coupled to the plunger 106a with pin 130a. In this situation, as the release tab 104a is rotated in a counterclockwise direction, one end of the release tab 104a approaches a wall of the housing 102 while the opposite end of the release tab moves away from the housing wall and toward the protrusions in the plunger (not shown in this figure, but seen in FIG. 1E, for example). Rotation in the opposite direction (clockwise) results in the opposite motion of the release tab. When the end of the release tab presses against the housing wall, the plunger 106a is forced outward and away from the housing retracting the plunger out of the housing channel and away from the housing 102. The position of the plunger may be adjusted as desired, such as to a position where the suture slots on the plunger align with the suture slots on the housing to release the suture and allow the suture to move. Over-rotation of the release tab is prevented by the protrusions 312 on the plunger (not shown in FIG. 6F, but illustrated in FIG. 1E). Other aspects of the housing 102 and plunger 106a are generally the same as previously described with respect to housing 102 and plunger 106a in this specification.

When actuation of the release tab and plunger are completed, the release tab may be realigned and placed back in the flat configuration so that it lays flat against the plunger. The plunger may then be pressed and advanced back into the housing channel to close the device and lock suture filaments when desired. Actuation of the release tab to retract the plunger from the housing may be repeated as needed.

Figure 7:
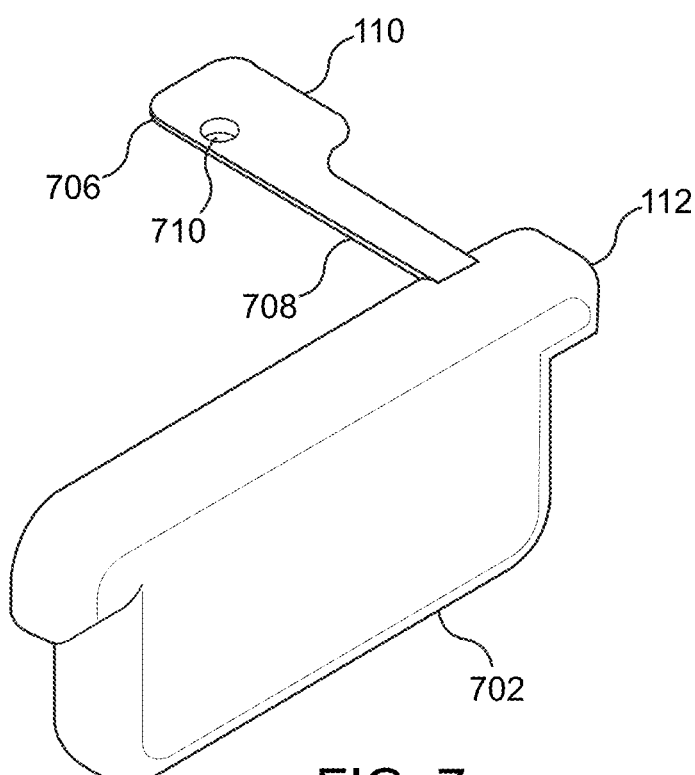
FIG. 7 shows a perspective view of an example of a stop element.

FIG. 7 shows the stop element 112 and the release tab 110 coupled to the stop element 112. The stop element as previously discussed provides a stop and prevents the cutter element from being actuated and inadvertently severing the suture filament. When the stop element 112 is removed, the cutter element may be actuated. The stop element has a rectangular body 702 with wings 704 that extend outward from either upper corner. The wings 704 are wide enough to sit on the shoulders 202 on the housing (see FIG. 2A). The release tab 110 is coupled to the stop element and includes an elongate arm 708 with an enlarged head region 706 that provides a larger area for grasping by the operator. In use, the operator can hold the enlarged head area and lift it up, thereby also lifting the stop element away from the housing thereby removing the stop element and allowing the cutter element to be actuated. The release tab may have adhesive on a bottom surface to help it stick to the housing and prevent it from unwanted movement. In this example, the release tab 706 includes an aperture 710 which receives a protrusion such as a pin (e.g. protrusion 220 in FIG. 2A) to help keep the release tab and stop element in place until the user wishes to actuate the cutter blade. The adhesive may be used alone or in combination with the aperture and protrusion example, or the apertures and protrusion may be used without adhesive. In other examples, the aperture and protrusion positions may be exchanged with one another so that the aperture is on the housing and the protrusion is on the release tab. Other shapes may be used for the stop element and the release tab, and these are not intended to be limiting.

Figure 8:
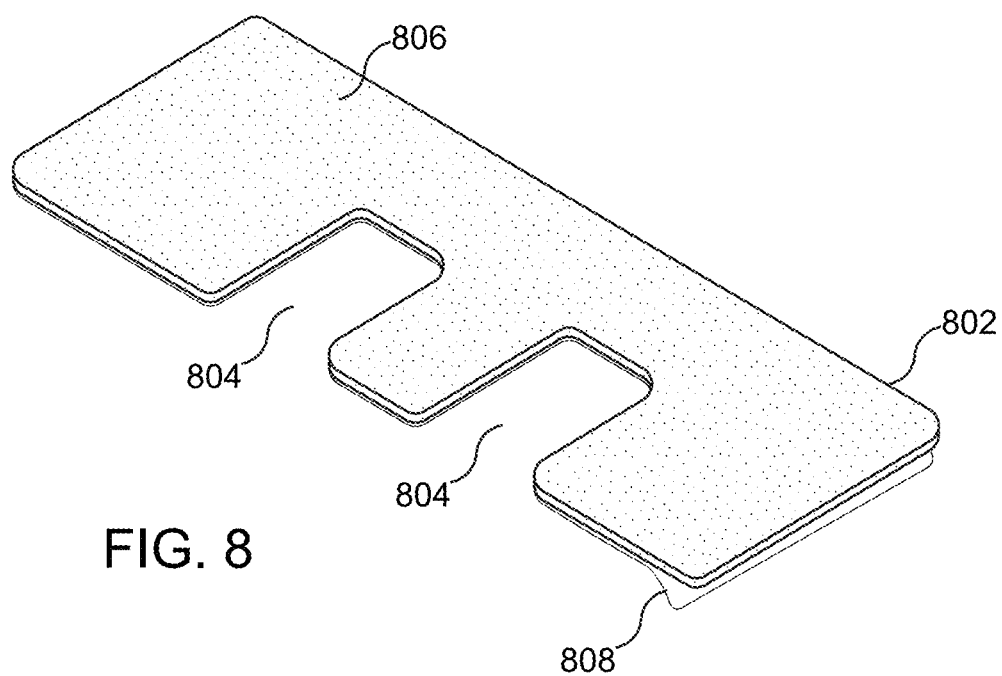
FIG. 8 shows a perspective view of an example of a substrate.

FIG. 8 shows an optional substrate 802 that may be placed on a bottom surface of the housing. The substrate may be rectangular in shape and have the same footprint that the bottom of the housing has. The substrate may include cutouts 804 that prevent the substrate from obstructing the housing suture slots. The upper surface of the substrate may be adhesively coupled to the bottom surface of the housing, or the substrate may be attached using other techniques known in the art. The substrate may be a soft resilient foam that provides a cushion and prevents trauma when the device is placed against the patient's skin and tension is applied to the suture filament. The substrate may also have an adhesive layer on the bottom surface to help adhere the device to the patient's skin. In that example, there may also be a backing layer 808 covering the adhesive which can be removed by peeling it way from the adhesive just before the device is applied to the patient's skin. In any example, the substrate 802 may also carry a therapeutic agent 806 that can be eluted from the substrate into the patient. For example, a pain reliever such as Lidocaine may be carried by the substrate and delivered to the patient to alleviate local pain. Or, an antibiotic may be eluted from the substrate layer to prevent infections around the wound site. Or combinations of therapeutic agents may be used.

FIGS. 9A-9M show an example of a method of use for any of the devices illustrated herein. The example is primarily directed at using the devices disclosed herein to secure tension in a suture to close a vascular access site into a blood vessel such as a vein or artery. This is not intended to be limiting, and one of skill in the art will appreciate that the devices disclosed herein may be used in other applications. Additionally, as previously mentioned, the device may be provided alone or with one or more sutures. A few other examples will be disclosed below.

Figure 9A:
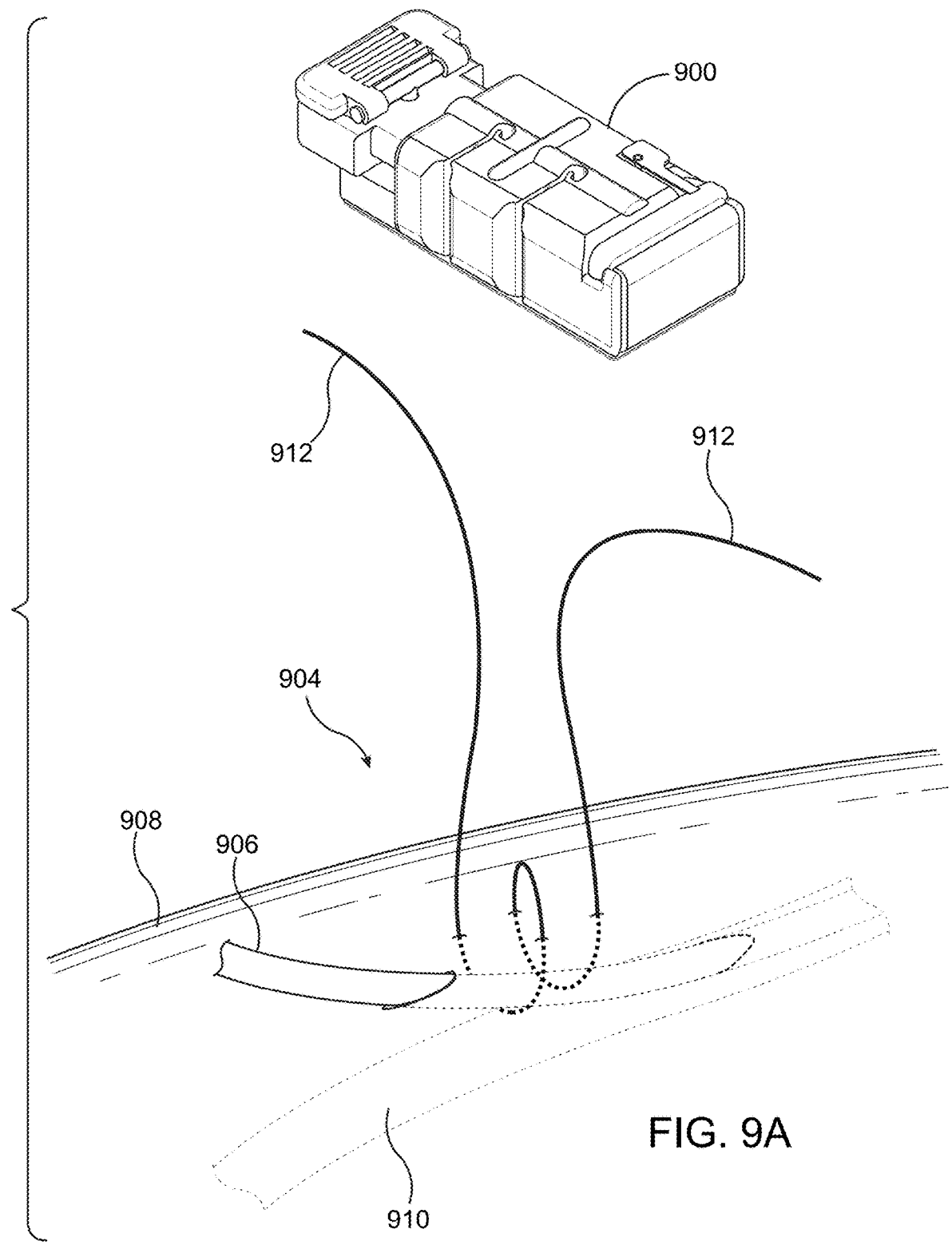
FIGS. 9A-9M show an example of a method of closing a wound with a suture retention device.

In FIG. 9A, the suture retention device 902 which may be any of the devices disclosed herein is used to help close a vascular access site 904 in a patient after a catheterization procedure or other medical procedure which accesses the vasculature. Note that the device may be supplied in the open or closed configuration, but FIG. 9A shows the device in the open configuration where the plunger is retraced out of the housing so that the housing suture slots are aligned with the plunger suture slots. This will be illustrated more clearly below. The vascular access site 904 may include a catheter or sheath or other vascular device 906, or both, which is introduced percutaneously or via cut down through the patient's skin 908 into a blood vessel 910 such as a vein or artery. A suture 912 may be applied to the vascular access site to help facilitate closure of the wound after the procedure is complete. For example, the suture 812 may be applied using a figure-of-eight pattern where a first loop is disposed on one side of the device 906, through the tissue and under the device 906 to exit the tissue on the opposite side of the device. The suture filament is then crossed at an angle over the tissue surface to the first side of the device upstream or downstream of the first loop then inserted back into the tissue and through the tissue to the opposite side of the device where the suture filament exits the tissue leaving a second loop in the tissue and two free ends exposed outside the tissue. The second loop may or may not be disposed under the device. Generally, both loops also do not loop under the blood vessel. The two free ends 912 may then be tied together forming an "X" shaped pattern on the top of the skin and also forming the figure-of-eight. This suture pattern is commonly used to close vascular access sites. However, in this example, the free ends will not be tied together and the suture retention device will be used to secure the free ends. Thus, this example of a method is a knotless method or knot-free method. When the filament is tensioned and the free ends are tied together or otherwise secured, the resulting compression in the skin closes the wound in the skin as well as applies compression to the access point in the vessel which is adequate to seal the wound and prevent blood leakage. A suture is commonly used when the wound site does not close using traditional application of pressure, or to ensure that the wound remains closed even after pressure has been applied.

Figure 9B:
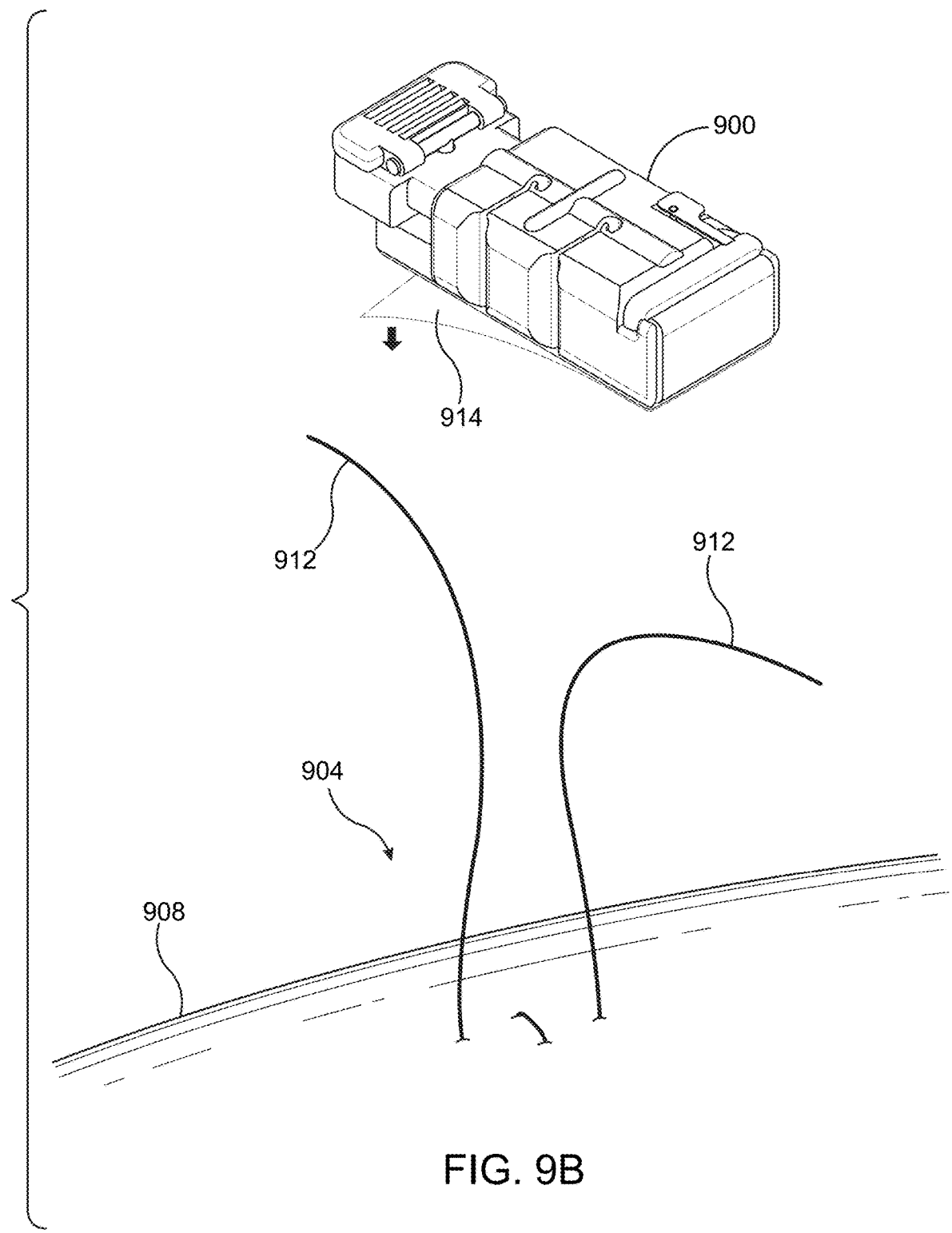

In FIG. 9B, the figure-of-eight suture has been sutured into the patient and the catheter, sheath or other device has been removed. The two free ends 912 are not tied together and remain free ends. The suture retention device 900 is advanced toward the free ends 912. The suture retention device is in the open position where the plunger is retracted from the housing far enough so that the plunger suture slots align with the housing suture slots. Optionally, a substrate layer maybe included with the suture retention device 900 and the backing layer 914 may be peeled away from the substrate at this time or later on in the process when desired.

Figure 9C:
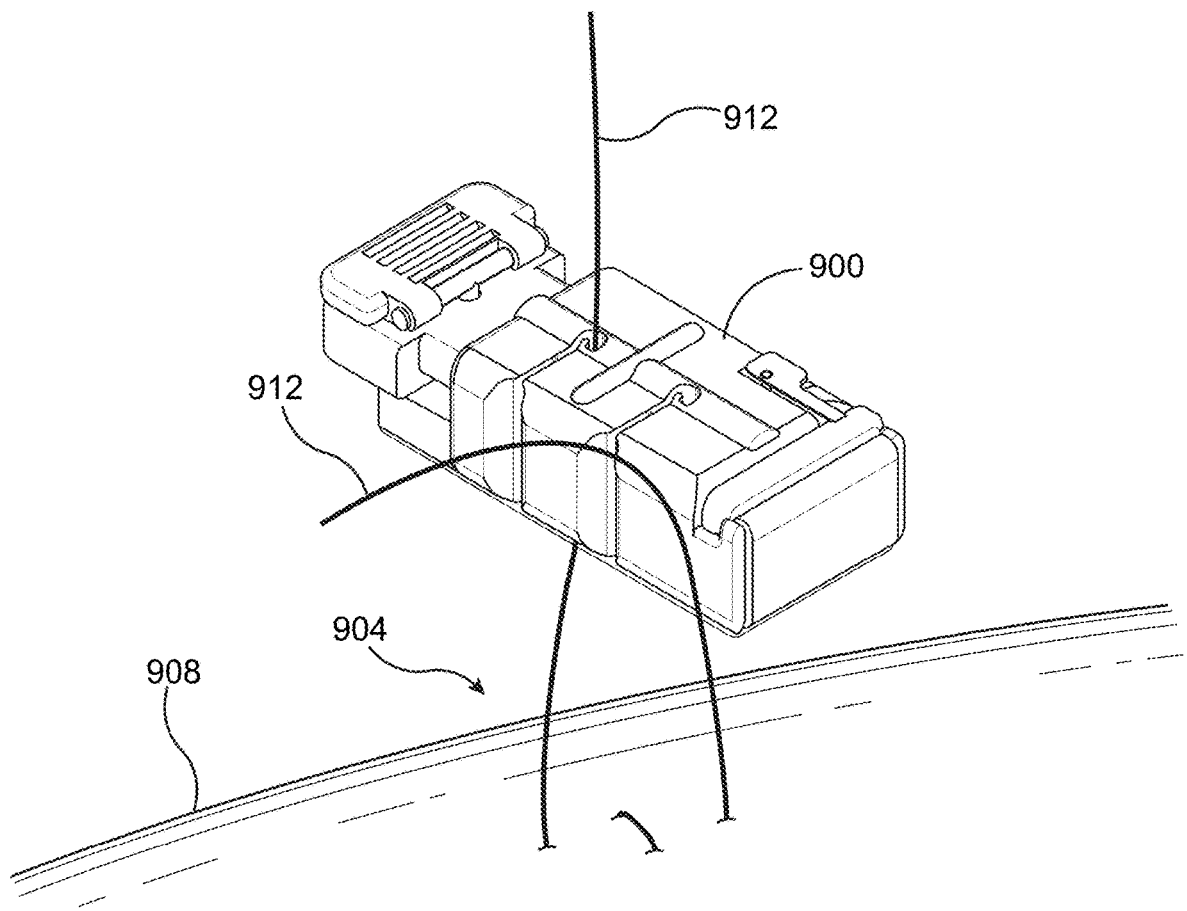

In FIG. 9C, one of the free ends 912 is disposed through a first plunger suture slot and a first housing suture slot (which are aligned with one another) and advanced into the enlarged head region of the suture slots to help hold it in position.

Figure 9D:
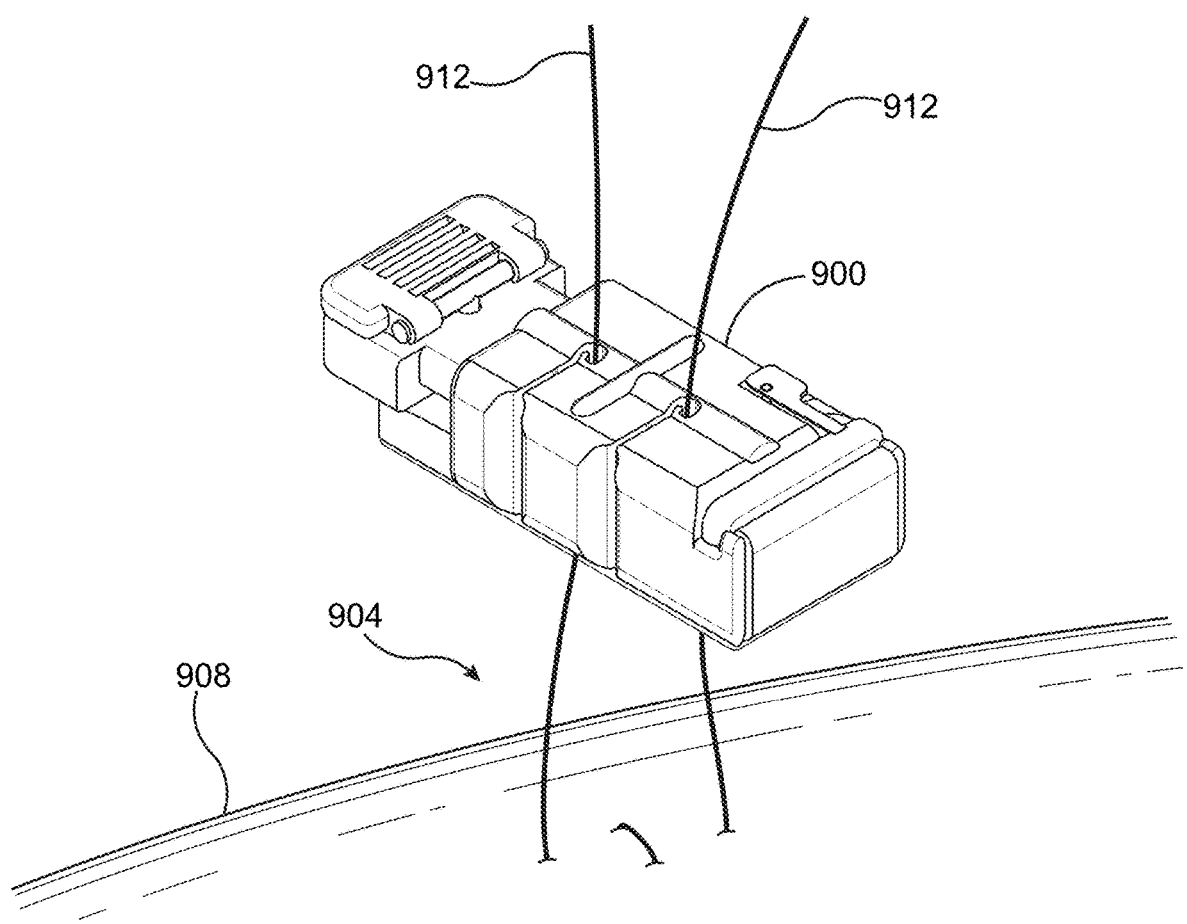

FIG. 9D shows the second of the free ends 912 is disposed through a second plunger suture slot and a second housing suture slot (which are aligned with one another) and then advanced into the enlarged head region of the suture slots to help hold it in position.

Figure 9E:
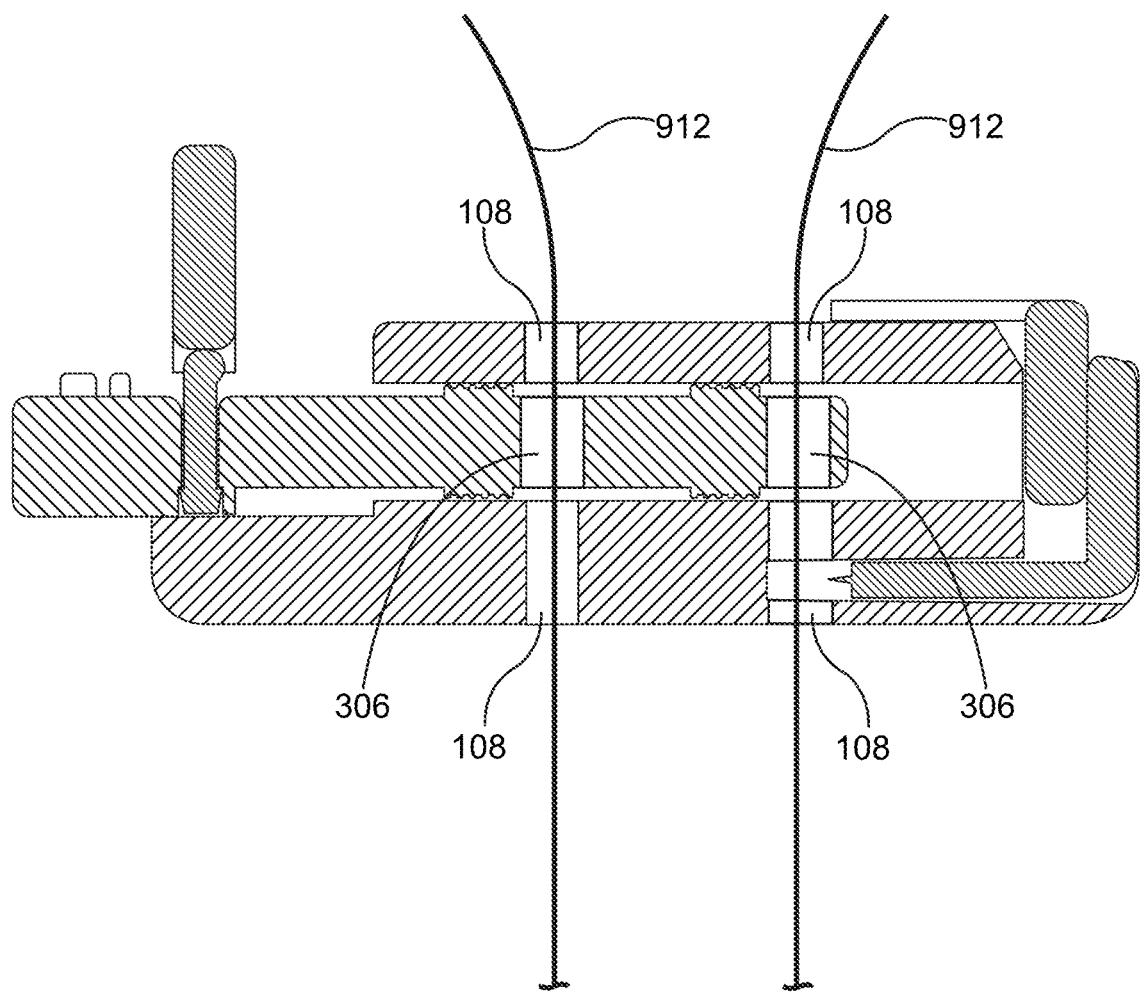

FIG. 9E shows a cross-section of FIG. 9D taken along the longitudinal axis of the device. Suture filaments 912 pass easily through both the housing suture slots 108 and the plunger suture slots 306 because they are aligned with one another. Other aspects of the suture retention device are the same as described above.

Figure 9F:
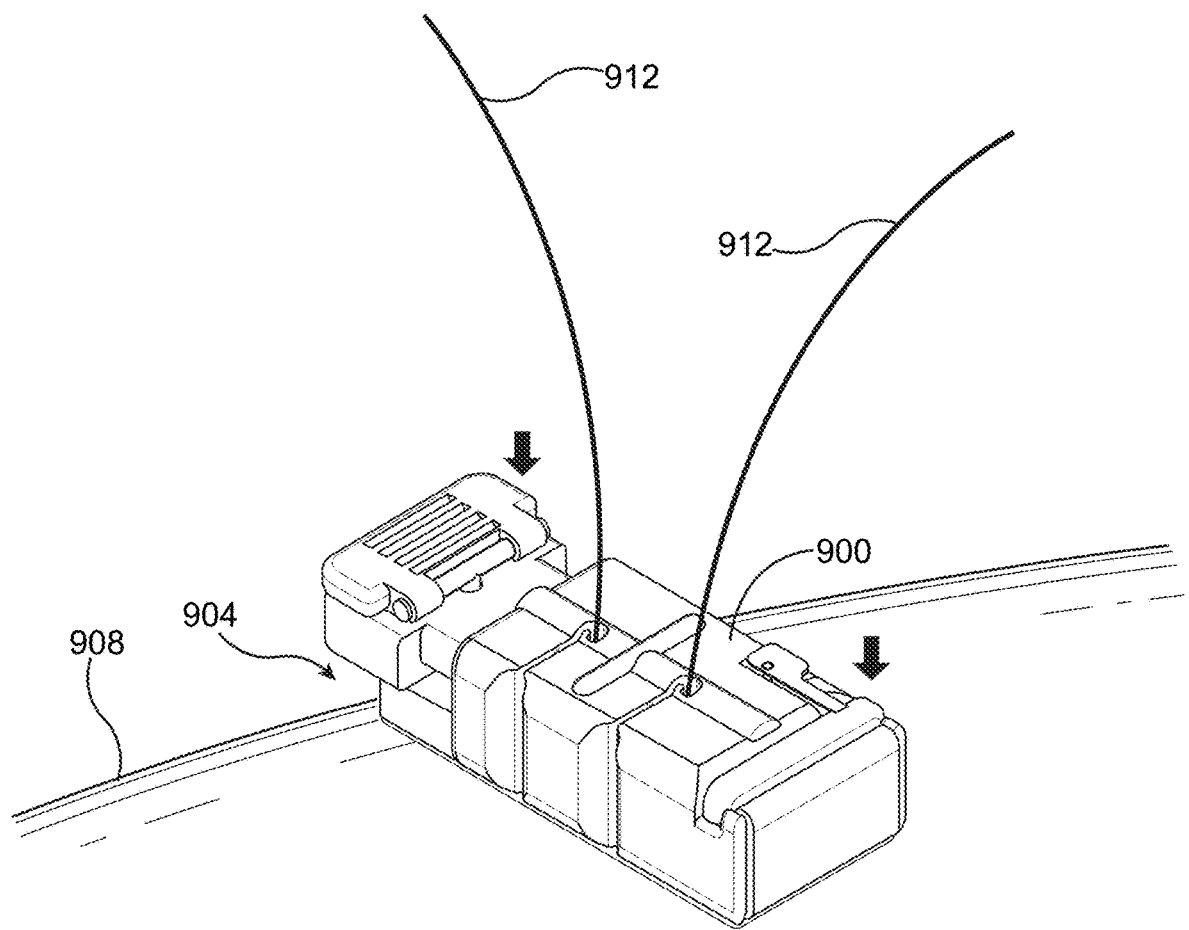

FIG. 9F shows that once both filaments are disposed in their respective suture slots, the suture retention device 900 may then be slidably advanced over both free ends and toward the wound site 904 until the suture retention device abuts the patient's skin.

Figure 9G:
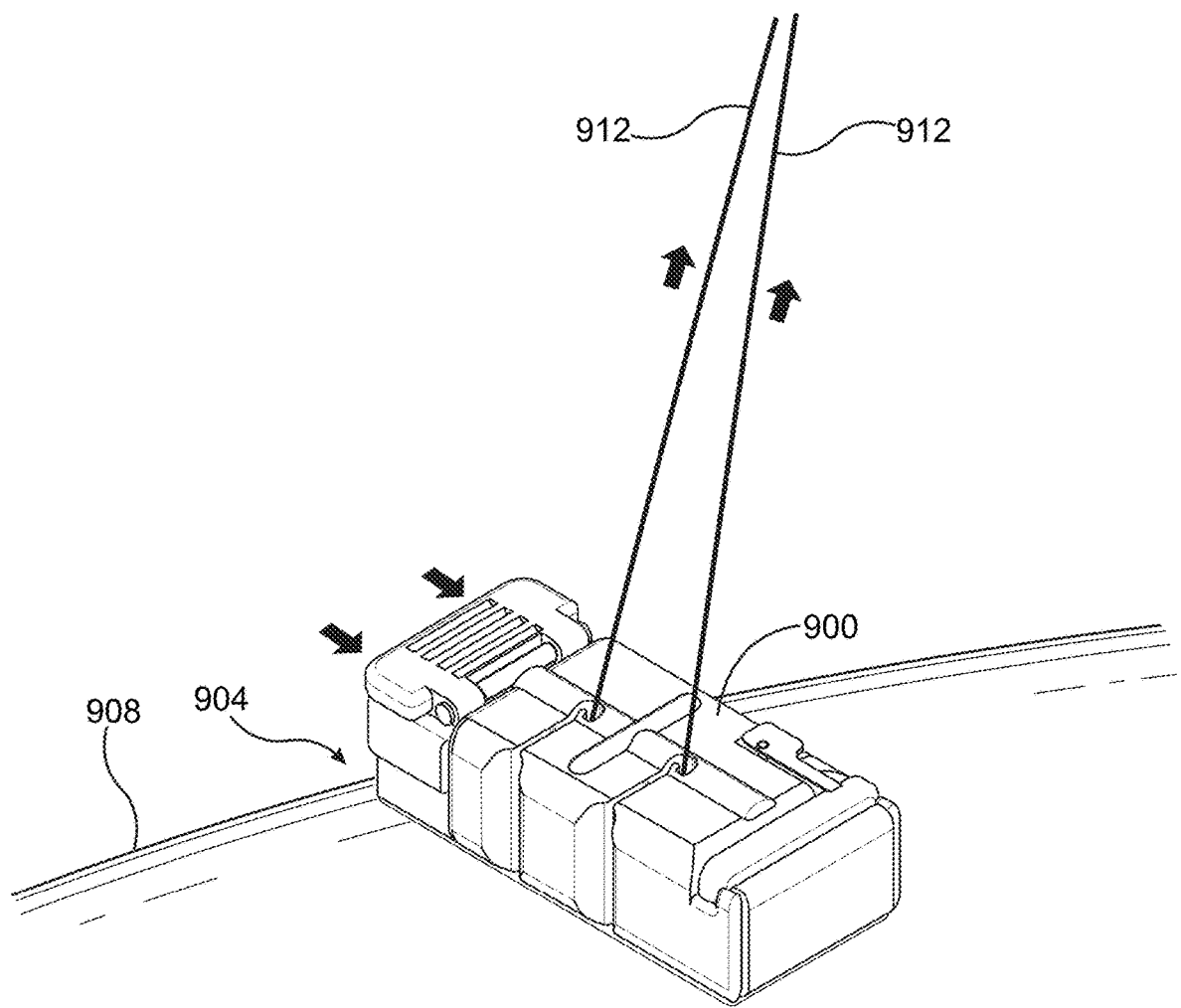

In FIG. 9G, tension is applied to both free ends 912 of the suture filament to ensure that the suture retention device 900 is firmly apposed with the patient's skin and the figure-of-eight suture closes the wound and applies adequate compression to the tissue to close the puncture site in the vessel. Once the operator is satisfied with the tension in the suture filament, the operator may close the suture retention device by pushing the plunger into the plunger channel in the housing so that the plunger suture slots are misaligned with the housing suture slots thereby creating an interference fit between the suture filament, the plunger and the housing which captures the suture filament and prevents it from moving which maintains the tension in the suture.

Figure 9H:
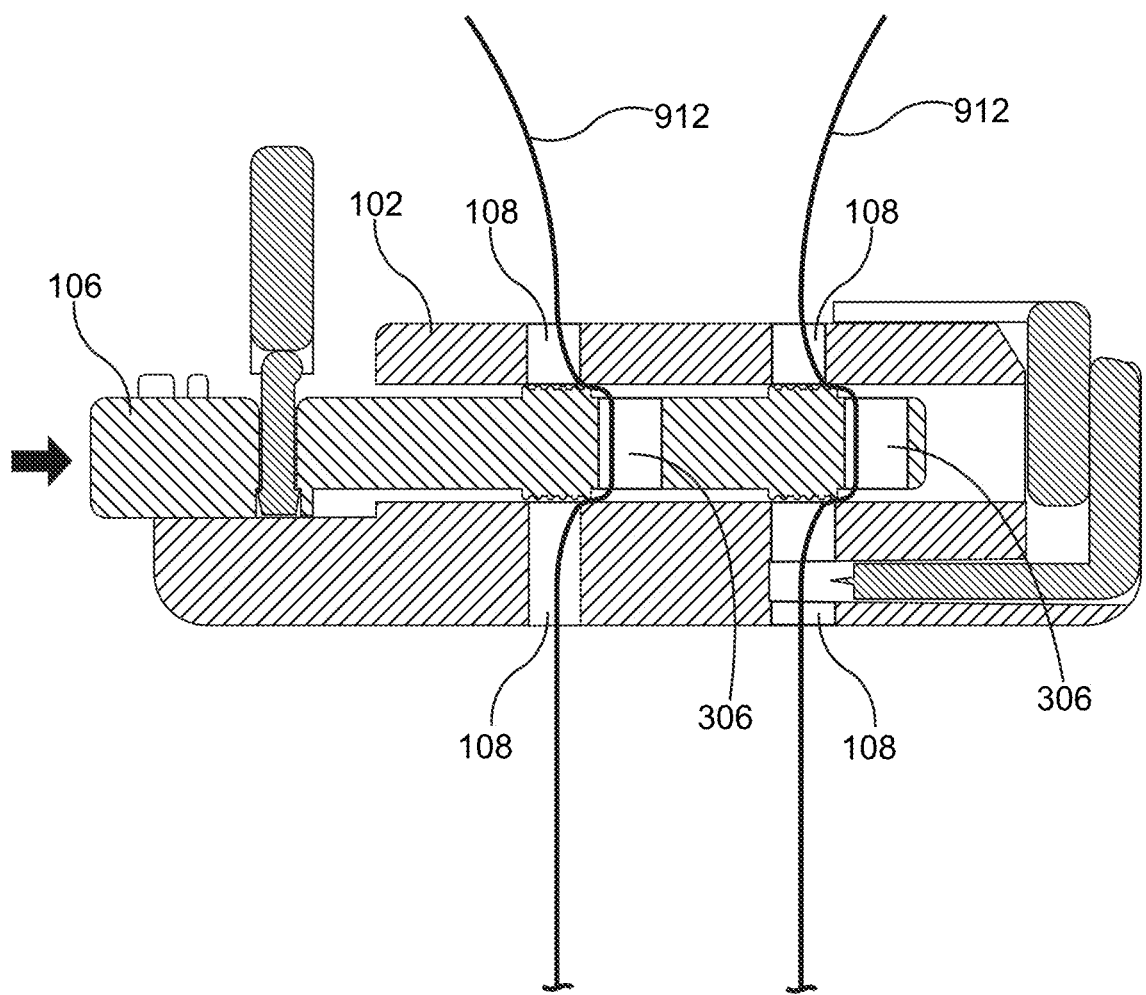

FIG. 9H shows a cross-section of FIG. 9G taken along the longitudinal axis of the device. Once the plunger 106 is pushed into the housing 102 so the device is in a closed configuration, the suture is captured between the housing and the plunger surface to form an interference fit which prevents movement of the suture filament 912. The interference fit is created because the housing suture slots 108 are no longer aligned with the plunger suture slots 306.

Figure 9I:
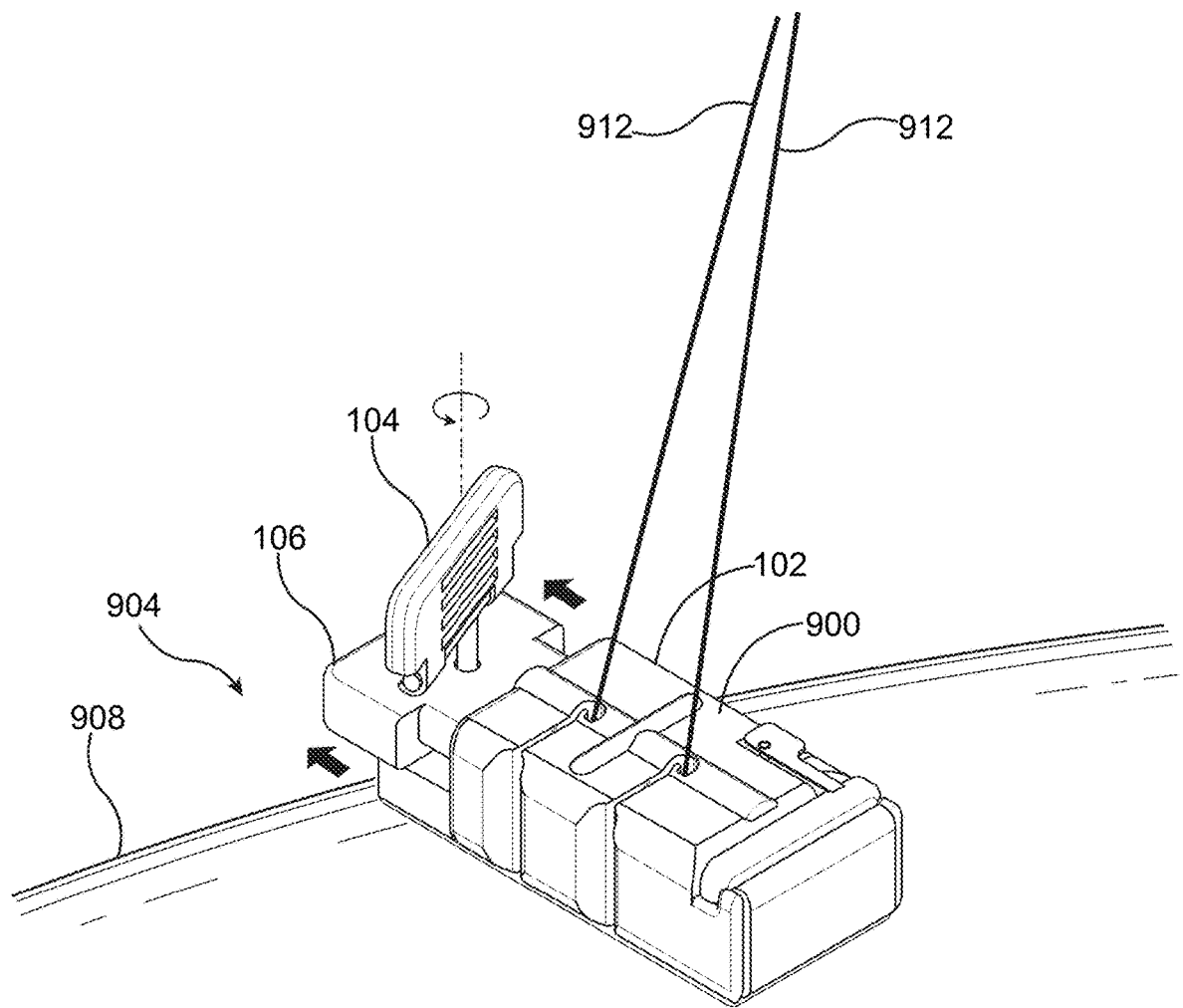

FIG. 9I shows release of the plunger 106 from the housing 102. In some circumstances, the operator may wish to return the device to an open configuration from the closed configuration. For example, the operator may wish to reposition the device or adjust tension in the suture filaments 912. Thus, release tab 104 may be actuated as previously described above in FIGS. 1D-1E and FIGS. 6A-6C where the release tab is rotated upward from a flat position into a vertical position and then rotated about its vertical axis so that one end of the release tab abuts the housing thereby retracting the plunger 106 from the housing 102 and realigning the plunger suture slots with the housing suture slots. The device may then be repositioned or tension in the suture adjusted.

Figure 9J:
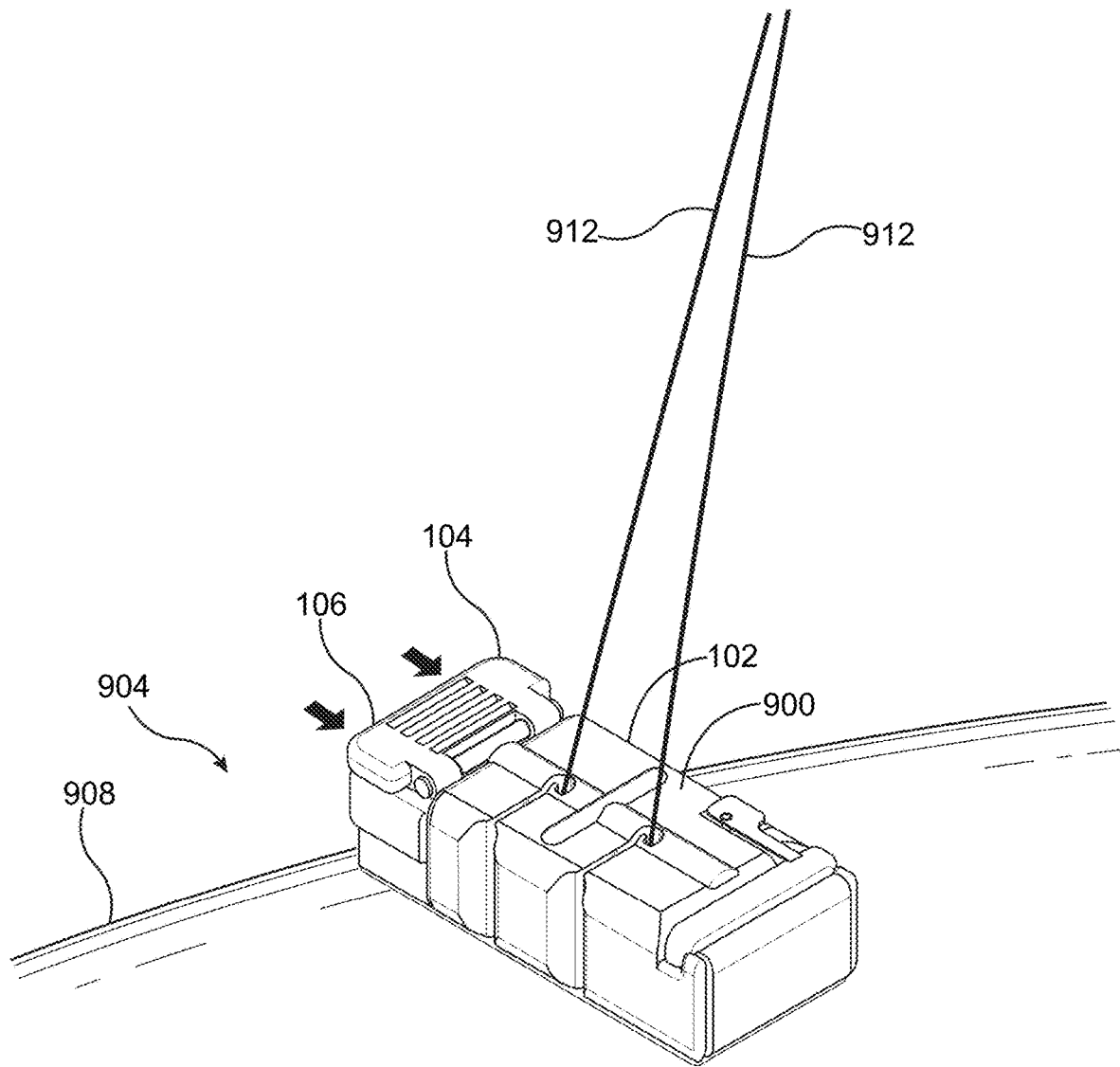

FIG. 9J shows that once the device is repositioned and suture tension adjusted to a desired level, the device may be re-closed. Here, the plunger is pushed back into the housing so that the housing suture slots are misaligned with the plunger suture slots are previously described above in FIGS. 9G-9H.

Figure 9K:
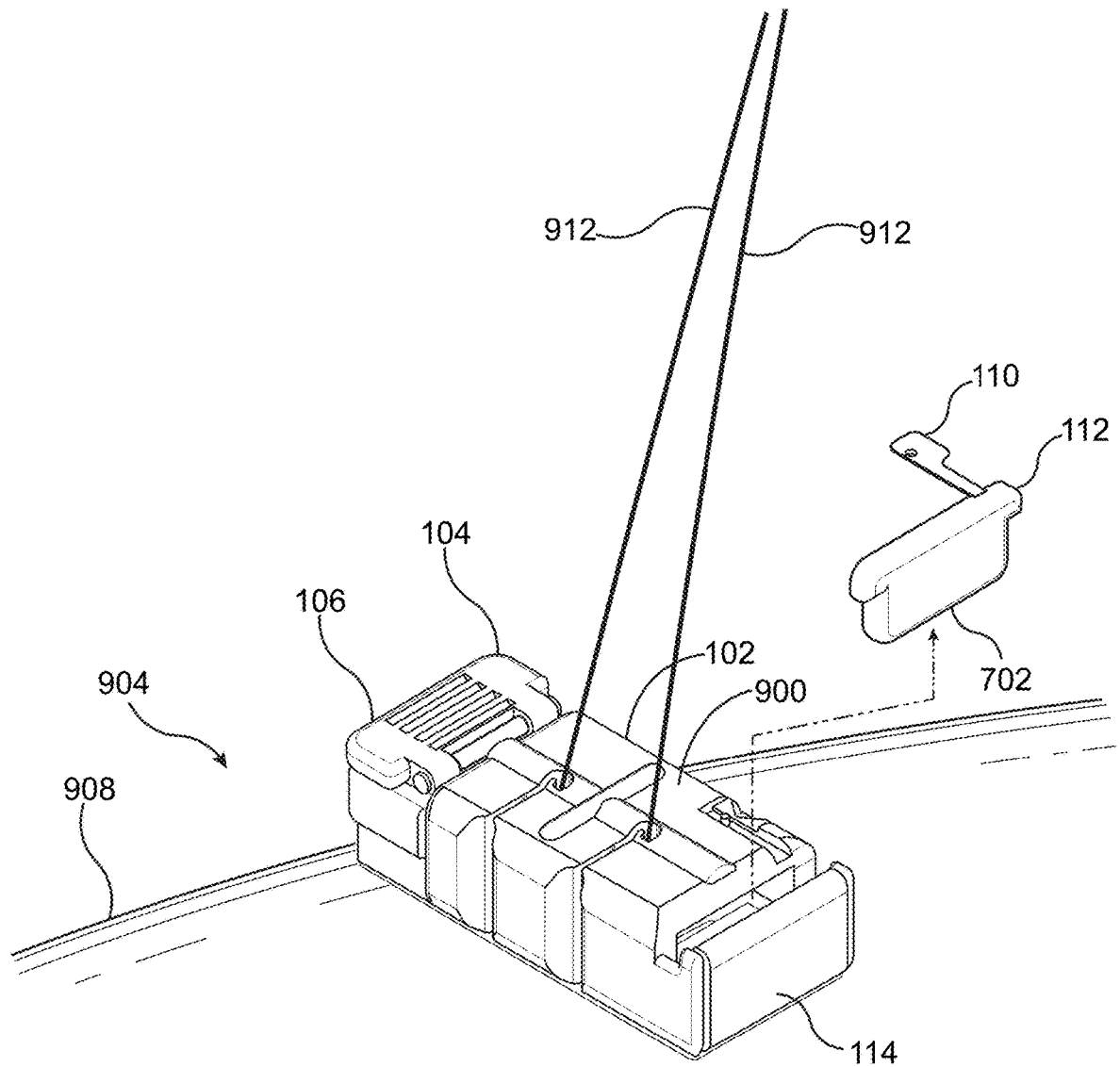

FIG. 9K shows removal of the stop element 702 from the housing 102. After the suture and suture retention device have been properly re-positioned and suture tension re-adjusted, the user closes the plunger as described above. The suture filament is captured in the suture retention device and the free ends of the suture filament extend from the housing allowing the vascular access site to close and begin healing. After the wound site has closed and any blood leakage from the wound site is stopped, the user can remove the stop element from the housing by lifting the cutter release tab 110 away from the protrusion in the housing and lifting the stop element away from the housing. The cutter element 114 is no longer constrained from being actuated by pushing it inward into the housing.

Figure 9L:
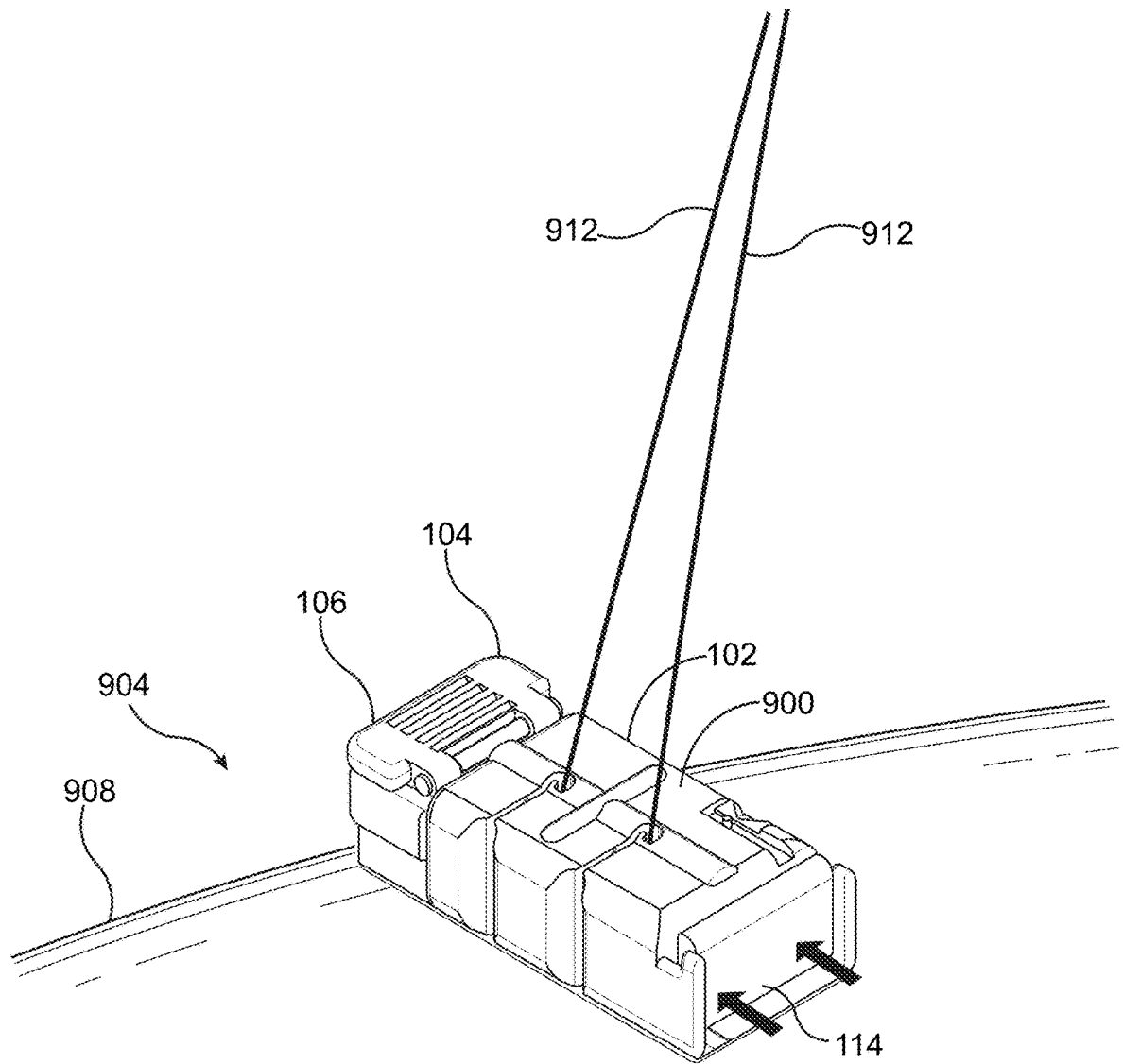

FIG. 9L shows advancement of the cutter element 114 into the housing cutter channel. Here, the user pushes the cutter element 114 into the housing along the cutter channel which pushes the cutter blade against one of the suture filament free ends 912 thereby severing it.

Figure 9M:
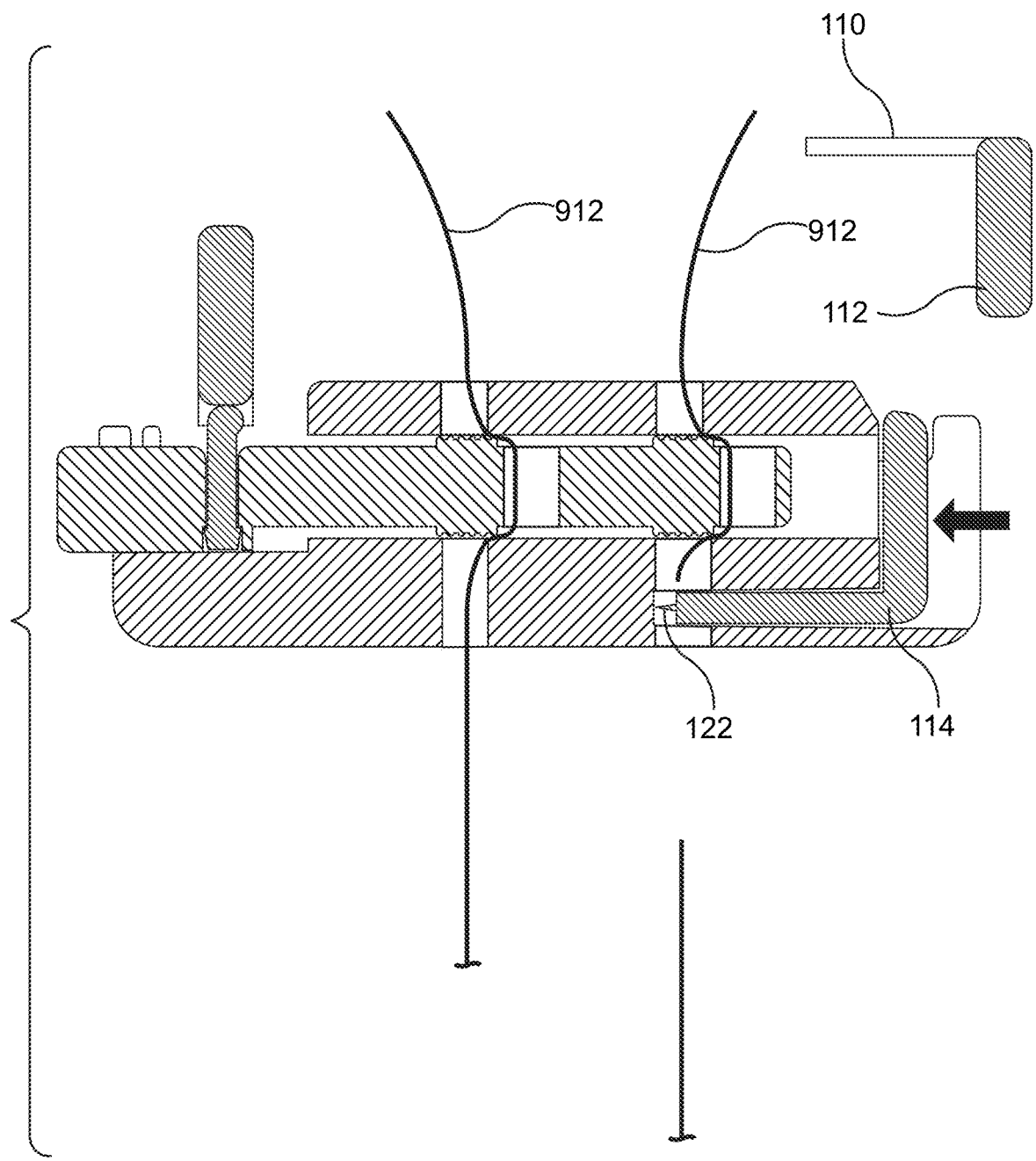

FIG. 9M shows a cross-sectional view of FIG. 9L taken along the longitudinal axis of the device and more clearly illustrates cutting of the free end of the suture filament. Here, the filament free end closest to the cutter blade is severed by blade 122 when the user pushes in the cutter element 114 along the channel 210 (best seen in FIG. 2A). The other free end remains intact and uncut. In other examples, both free ends may be severed by one or more cutting blades. The severed free end is still attached to the suture retention device because it is pinched between the plunger and the housing, but the remainder of the free end is left in the tissue. The blade 122 is disposed very close to the bottom of the suture retention device housing, therefore when the free end is severed, the amount of suture extending out of the tissue on that side is minimal, and the suture is then substantially flush with the patient's skin, or only a 1 mm or less or 2 mm or less extends out of the skin. The less suture that remains, the easier it is to pull the suture through the skin during suture removal which is quicker and less painful. The other free end of the suture also is still attached to the suture retention device so that when the suture retention device is pulled upward and away from the patient, the suture filament is pulled out of the patient leaving no suture behind in the patient. Thus, cutting the suture free end allows the user to remove the suture from the wound. The user may be a physician or other healthcare worker in a clinic or hospital, or the user may be the patient who removes the suture at home.

Examples of Stitch Patterns

FIGS. 10A-10D illustrate a wound and several examples of suture stitching patterns that may be used with any of the suture retention devices disclosed herein to help close the wound. These stitching patterns are not intended to be limiting and other stitching patterns may be used.

Figure 10A:
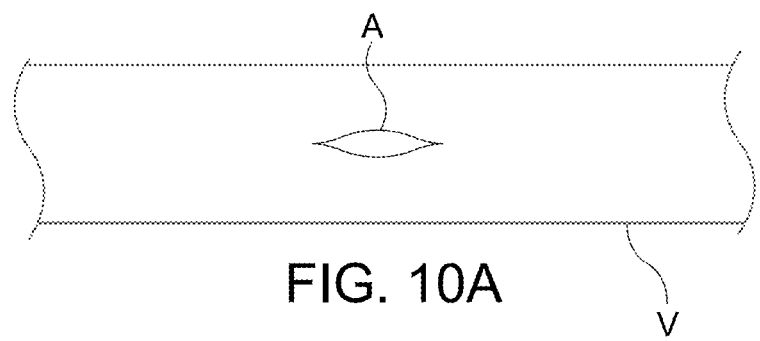
FIG. 10A shows an example of a vascular access site.

FIG. 10A illustrates a blood vessel V, such as a vein or artery with an access site A formed in the vessel. The access site is where a guidewire, introducer sheath, catheter or other device is inserted into the vessel.

Figure 10B:
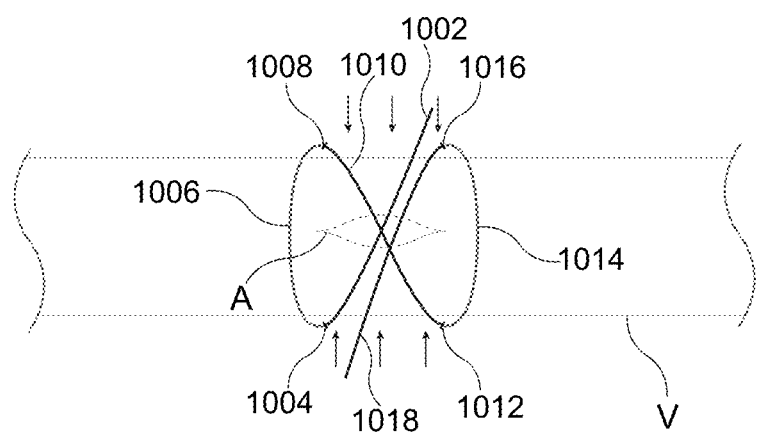
FIG. 10B shows an example of a figure-of-eight stitch pattern.

FIG. 10B illustrates an example of the figure-of-eight stitch that has been discussed above and more clearly illustrates the stitch pattern. Here, the suture filament has a first free end 1002. The suture enters the tissue at a point 1004 laterally away from an edge of the blood vessel or adjacent the blood vessel and longitudinally adjacent the access site A. The suture passes through the tissue above the blood vessel (the suture does not pass under the blood vessel otherwise when the suture is tensioned it will collapse the blood vessel) and crosses 1006 over the blood vessel and exits the tissue 1008 at a position laterally away from the opposite edge of the blood vessel or otherwise adjacent the blood vessel and longitudinally adjacent the access site A. The filament then crosses 1010 back over the access site forming the first loop in the figure-of-eight, and re-enters the tissue at a point 1012 that is similarly disposed laterally away from the edge of the blood vessel or adjacent the blood vessel, and longitudinally adjacent the access site but axially offset from the first loop. Again, the filament passes through the tissue on top of the blood vessel and across the blood vessel 1014 to exit the tissue at point 1016 that is also laterally disposed away from the blood vessel or otherwise adjacent the blood vessel while longitudinally spaced adjacent the access site but axially offset from the first loop. The second free end 1018 may then be passed over and across the access site forming the second loop in the figure-of-eight. The two free ends can then be tied together to close the stitch or any of the suture retention devices disclosed herein may be used to secure the free ends thereby forming the figure-of-eight pattern with two loops. When tension is applied to the free ends and the loops in the stitch close, a compressive force indicated by the arrows pointing inward toward the blood vessel tighten the tissue to close the wound and access site. Thus, in this example the compressive force is applied in a direction that is transverse or orthogonal to the longitudinal axis of the blood vessel, so the compressive forces are applied inward toward the longitudinal axis of the blood vessel.

Figure 10C:
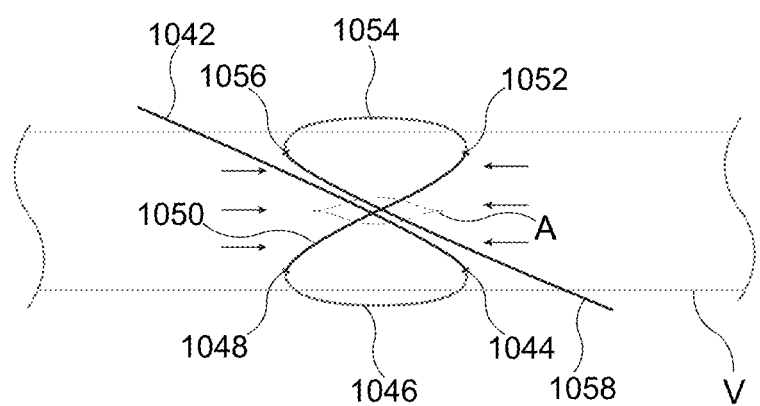
FIG. 10C shows an example of a figure-of-infinity stitch pattern.

FIG. 10C illustrates a sideways figure-of-eight stitch which may also be referred to as a figure-of-infinity stitch pattern. It is substantially the same as the figure-of-eight pattern described previously with the major difference being that the figure-of-eight stitch is rotated ninety degrees either clockwise or counterclockwise and the compressive forces are provided by the figure-of-eight stitch are also rotated ninety degrees and they are directed inward toward the center point of the stitch and along the longitudinal axis of the blood vessel.

As before, the blood vessel V, such as a vein or artery has an access site A formed in the vessel. The access site is where a guidewire, introducer sheath, catheter or other device is inserted into the vessel.

In this example, the figure-of-infinity stitch pattern is used to close the wound. It may be used with any of the suture retention devices disclosed herein or it may be manually tied. The figure-of-infinity pattern may be used alone, or in combination with a figure-of-eight pattern, or with any other stitch pattern. The suture filament has a first free end 1042 that crosses over the access site from one edge of the blood vessel to the opposite edge of the blood vessel. The suture enters the tissue at a point 1044 laterally adjacent an edge of the blood vessel or laterally away from an edge of the blood vessel and longitudinally adjacent the access site A. The suture passes through the tissue above the blood vessel (the suture does not pass under the blood vessel otherwise when the suture is tensioned it will collapse the blood vessel) and then extends substantially parallel with the longitudinal axis of the blood vessel 1046 and exits the tissue 1048 at a position axially displaced away from the initial entry point 1044 and laterally adjacent an edge of the blood vessel or laterally away from the edge of the blood vessel. The filament then crosses 1050 back over the access site and re-enters the tissue at a point 1052 that is similarly disposed laterally adjacent the edge of the blood vessel or laterally away from the edge of the blood vessel and longitudinally adjacent the access site. Again, the filament passes through the tissue on top of the blood vessel and extends substantially parallel with the longitudinal axis of the blood vessel 1054 to exit the tissue at point 1056 that is also laterally disposed away from the edge of the blood vessel or laterally adjacent the edge of the blood vessel, while longitudinally spaced adjacent the access site but axially displaced away from the second insertion point 1052. The second free end 1058 may then be passed over and across the access site. The two free ends can then be tied together to close the stitch or any of the suture retention devices disclosed herein may be used to secure the free ends thereby forming the sideways figure-of-eight pattern also referred to as the figure-ofinfinity pattern. When tension is applied to the free ends and the loops in the stitch close, a compressive force indicated by the arrows pointing inward toward the access site and substantially parallel with the longitudinal axis of the blood vessel tighten the tissue to close the wound and access site. Thus, in this example the compressive force is applied in a direction that is substantially parallel to the longitudinal axis of the blood vessel, so the compressive forces are applied inward along the longitudinal axis of the blood vessel.

Figure 10D:
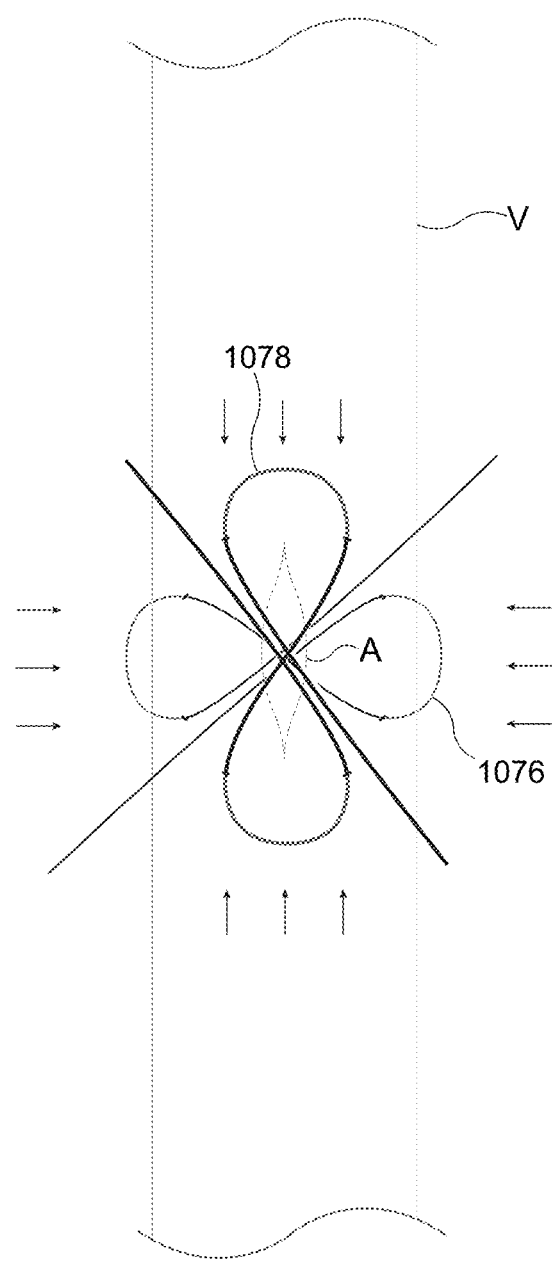
FIG. 10D shows and example of both stitch patterns from FIGS. 10B-10C used to close a wound.

FIG. 10D illustrates a combination of a figure-of-eight stitch pattern described in FIG. 10B and a figure-of-infinity stitch pattern described in FIG. 10C used to close an access site A in a blood vessel V. Here, two suture filaments are used to form the two stitch patterns which results in four free ends that can then be either tied together to close the stitch or two pairs of free ends can be secured with one or two suture retention devices such as those described herein. Here, the figure-of-eight stitch pattern 1078 and the figure-of-infinity stitch pattern 1076 are the same are previously described above and the corresponding detailed description are not repeated for the sake of brevity. The resulting stitch pattern is then appropriately tensioned and closed to provide compressive forces in both the axial direction inwardly along the longitudinal axis of the blood vessel and also inwardly toward the access site in a direction that is transverse to, or orthogonal to the longitudinal axis of the blood vessel, as indicated by the arrows.

Other Examples of Suture Retention Devices

Figure 11:
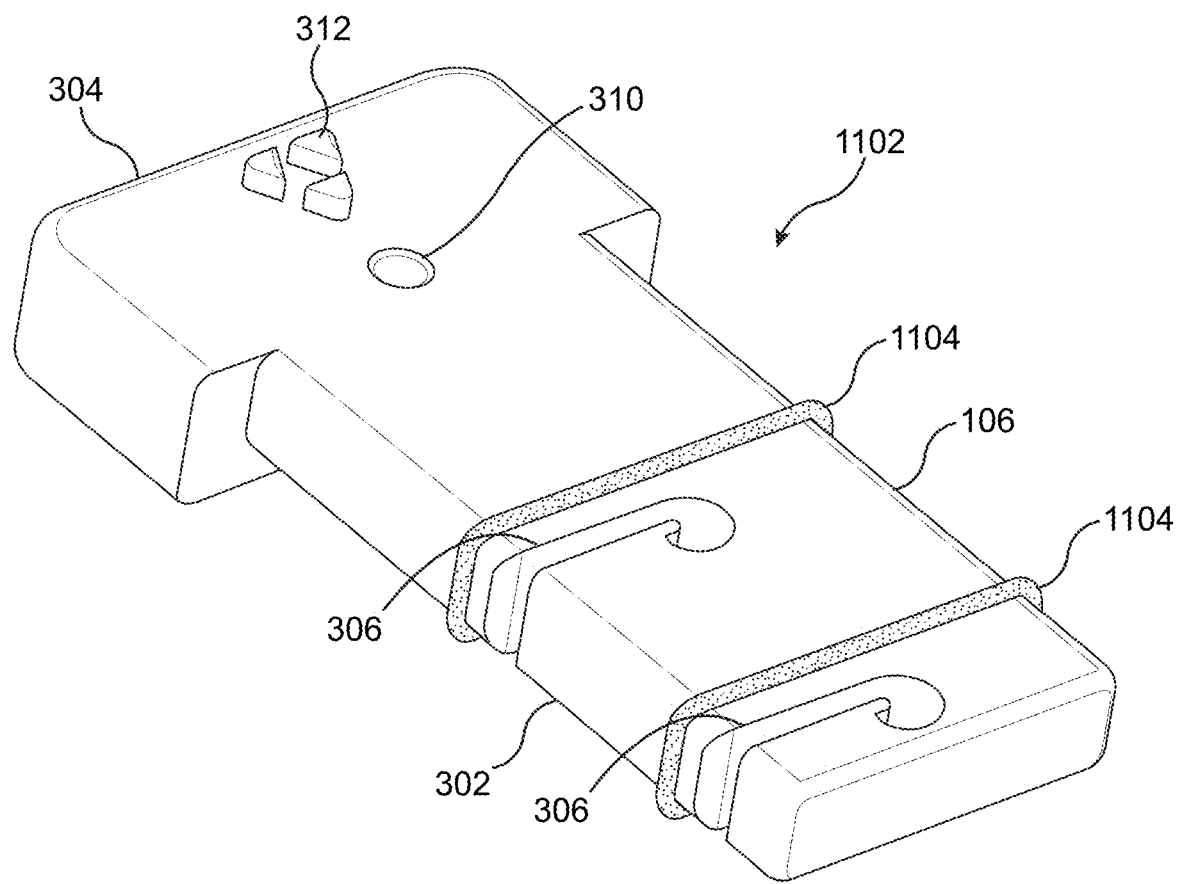
FIG. 11 illustrates a perspective view of another example of a plunger.

FIG. 11 illustrates an example of an alternative plunger 1102 design. Here, the plunger 1102 is generally the same as the plunger 104 previously described above (see e.g. FIGS. 1B, FIG. 3 and FIG. 4) with the major difference being that the surface textured ribs or ridges 308 on the top and bottom surfaces of the plunger have been removed and replaced with circumferential rings 1104 which are disposed circumferentially around the plunger to help provide the interference fit between the plunger, the housing and the suture filament to prevent movement of the suture filament. The circumferential rings may be O-rings or other soft resilient rings wrapped around the plunger adjacent one or both of the plunger suture slots 306. In this example, two circumferential rings are used. Other aspects of plunger 1102 are generally the same as plunger 104 previously described above. Plunger 1102 is used with the housing 102 previously described above in the same manner that plunger 104 is used with housing 102 therefore the method of use described in FIGS. 9A-9M and the stich patterns described in FIGS. 10A-10D are also applicable to the use of plunger 1102. The plunger of FIG. 11 may be used with any of the housings disclosed herein.

Figure 12:
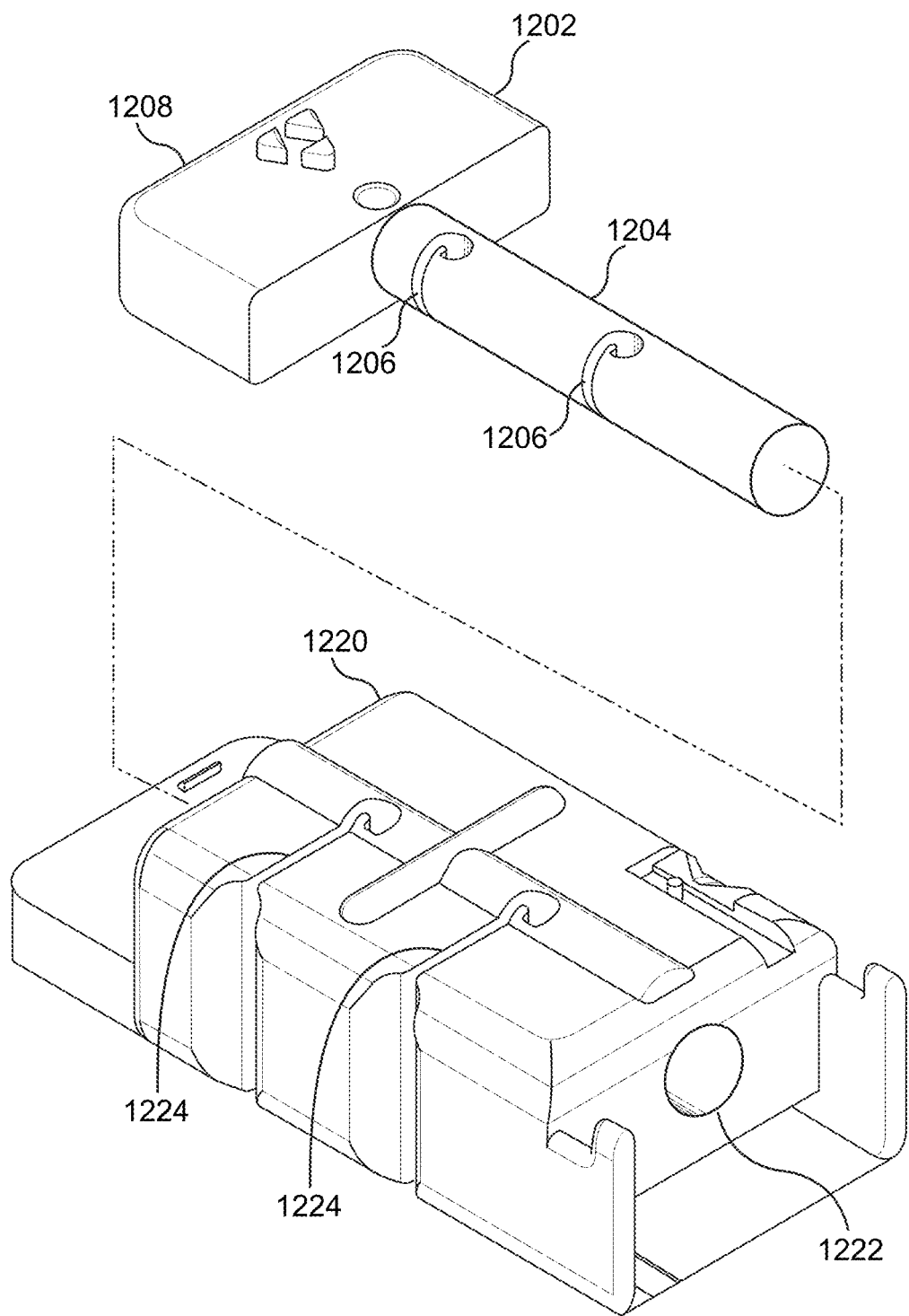
FIG. 12 illustrates perspective view of another example of a suture retention device.

FIG. 12 illustrates another example of a suture retention device with a plunger 1202 and a housing 1220 that cooperate with one another to secure suture filaments together.

In FIG. 12, the plunger 1202 includes an enlarged head region 1208 and an elongate and narrower cylindrical shaft 1204 to form a T-shaped plunger. The shaft 1204 includes one or two, or more plunger suture slots 1206 which have an elongate portion coupled to an enlarged head portion for holding onto the suture filament. Therefore, the major difference in this example and plunger 104 previously described is that instead of the narrow rectangular plunger portion of plunger 104, the plunger now has been modified to replace the rectangular plunger portion with a cylindrical plunger shaft. The cylindrical plunger shaft is received by a corresponding cylindrically shaped channel in the housing as seen in FIG. 12B. Other aspects of the plunger are generally the same as plunger 104 and are omitted here for the sake of brevity. The plunger may also include the release tab to help retract the plunger from the housing.

FIG. 12 also shows an example of a housing 1220 that cooperates with the plunger 1202 shown in FIG. 12A. Here, the housing 1220 includes a cylindrically shaped plunger channel 1222 that may extend all the way through the housing, or the channel may be open only at the plunger receiving end (the left side of FIG. 12) and closed at the opposite end, thus the channel is a blind hole. The housing suture slots 1224 are aligned with the plunger when the device is in the open position to receive the suture filaments and misaligned when the device is in the closed position to secure the filaments. Other aspects of the housing and use are generally the same as previously discussed with respect to housing 102 and therefore, are omitted for the sake of brevity. For example, the housing may include the cutter, the cutter stop and the cutter release tab.

Other Uses of a Suture Retention Device

In the examples above, the suture retention devices and stitch patterns are described in terms of closing a wound after a medical procedure on a human. This is not intended to be limiting. One of skill in the art will appreciate that the suture retention devices and stitch patterns can be used on animals, or on cadavers or otherwise deceased humans. Additionally, the suture retention devices and stitch patterns may be used during practice or training sessions on materials other than tissue, for example foam, plastic, fruit or any other materials used during suture training (e.g. a synthetic material) so any number of materials may be sutured and the devices and methods described herein may be used. Additionally, the devices and methods described herein may also be used to secure the free ends of any filament, whether suture, or non-suture e.g. metallic filaments, other polymer filaments, tissue filaments, etc. Therefore, the devices and methods disclosed herein can be used in any medical or non-medical applications.

NOTES AND EXAMPLES

The following, non-limiting examples, detail certain aspects of the present subject matter to solve at least some of the challenges and provide at least some of the benefits discussed herein, among others.

Example 1 is a suture retention device, comprising: a housing having a channel extending therethrough; one or more housing suture slots disposed in the housing, the one or more housing suture slots configured to receive one or more suture filaments; and a plunger having one or more plunger suture slots disposed therein, the one or more plunger suture slots configured to receive the one or more suture filaments, wherein the plunger is slidably disposed in the channel of the housing, the plunger having an open position and a closed position, wherein in the open position, the plunger is partially disposed in the channel and the one or more housing suture slots are aligned with the one or more plunger suture slots to allow the one or more suture filaments to slidably move through the one or more housing suture slots and the one or more plunger suture slots, and wherein in the closed position, the plunger is disposed at a different position in the channel than in the open position, and the one or more housing suture slots are misaligned with the one or more plunger suture slots to prevent the one or more suture filaments from slidably moving through the one or more housing suture slots and the one or more plunger suture slots.

Example 2 is the device of Example 1, wherein in the closed position, the plunger is sized and shaped to create an interference fit between the plunger, a wall of the housing that defines at least a portion of the channel and the one or more suture filaments, the interference fit preventing movement of the one or more suture filaments through the one or more plunger suture slots and the one or more housing suture slots.

Example 3 is the device of any of Examples 1-2, further comprising a textured surface on a top surface or a bottom surface of the plunger, wherein the textured surface enhances the interference fit.

Example 4 is the device of any of Examples 1-3, wherein the housing has a longitudinal axis and wherein the channel is parallel with the longitudinal axis.

Example 5 is the device of any of Examples 1-4, wherein the housing has a longitudinal axis and wherein the one or more housing suture slots or the one or more plunger suture slots are transverse to the longitudinal axis.

Example 6 is the device of any of Examples 1-5, wherein the one or more housing suture slots or the one or more plunger suture slots are J-shaped.

Example 7 is the device of any of Examples 1-6, wherein the housing further comprises a cutter channel, and a cutting element slidably disposed in the cutter channel, the cutting element configured to cut at least one of the one or more suture filaments.

Example 8 is the device of any of Examples 1-7, wherein the cutting element comprises a sharpened blade coupled to a cutting block, and wherein the sharpened blade is disposed at an angle to apply a shear cutting force to the at least one of the one or more suture filaments.

Example 9 is the device of any of Examples 1-8, further comprising a stop element removably coupled to the housing, the stop element configured to prevent axial movement of the cutting element into the cutter channel.

Example 10 is the device of any of Examples 1-9, further comprising a protrusion and a recess, wherein one of the protrusion or the recess is formed in the housing and the other of the protrusion or the recess is formed in the cutting element, wherein the protrusion is received in the recess to prevent the cutting element from decoupling from the housing.

Example 11 is the device of any of Examples 1-10, further comprising a release tab coupled to the plunger, wherein actuation of the release tab applies a force against the housing to facilitate removal of the plunger from the channel.

Example 12 is the device of any of Examples 1-11, wherein the release tab pivots upward and away from an upper surface of the plunger, and wherein the release tab rotates about a central axis substantially orthogonal to the upper surface of the plunger.

Example 13, is the device of any of Examples 1-12, further comprising one or more protrusions extending from the plunger, the one or more protrusions configured to limit rotation of the release tab about the central axis.

Example 14 is the device of any of Examples 1-13, wherein the housing is clear to facilitate observation of the one or more suture filaments or observation of the plunger in the channel.

Example 15 is the device of any of Examples 1-14, further comprising a protrusion and a recess, wherein one of the protrusion or the recess is formed in the plunger and the other of the protrusion or the recess is formed in the housing, wherein the protrusion is received in the recess to prevent the plunger from falling out of the channel.

Example 16 is the device of any of Examples 1-15, further comprising a substrate layer coupled to a bottom surface of the housing.

Example 17 is the device of any of Examples 1-16, wherein the substrate layer comprises adhesive configured to bond the housing to a patient's skin, or wherein the substrate layer comprises a therapeutic agent configured to elute therefrom into the patient, or wherein the substrate comprises a foam configured to reduce or eliminate trauma to a patient's skin when the device is disposed thereagainst.

Example 18 is the device of any of Examples 1-17, wherein the therapeutic agent is configured to reduce pain or configured to reduce or eliminate infection.

Example 19 is a method for securing a suture filament, comprising: slidably disposing the suture filament into one or more plunger suture slots disposed in a plunger; slidably disposing the suture filament into one or more housing suture slots disposed in a housing; applying a tension to the suture filament; and moving the plunger into a channel in the housing so that the one or more plunger suture slots are misaligned with the one or more housing suture slots, thereby capturing the suture filament between the plunger and the housing and preventing movement of the suture filament relative to the plunger and the housing.

Example 20 is the method of Example 19, further comprising applying a tension to the suture filament and wherein the capturing of the suture filament maintains the tension in the suture filament.

Example 21 is the method of any of Examples 19-20, further comprising cutting the suture filament with a cutter element slidably disposed in a cutter channel in the housing.

Example 22 is the method of any of Examples 19-21, further comprising removing a catheter or a sheath from a blood vessel before cutting the suture filament.

Example 23 is the method of any of Examples 19-22, wherein cutting the suture filament comprises removing a stop element disposed between the cutter element and the housing thereby allowing advancement of the cutter toward the housing to cut the suture filament.

Example 24 is the method of any of Examples 19-23, wherein the suture filament comprises a first free end and a second free end, and wherein the cutting comprises cutting only one of the first free end and the second free end.

Example 25 is the method of any of Examples 19-24, wherein the cutting comprises cutting the suture filament so that it is substantially flush with a bottom wall of the cutter channel in the housing.

Example 26 is the method of any of Examples 19-25, further comprising removing the plunger from the plunger channel in the housing thereby aligning the one or more housing suture slots with the one or more plunger suture slots thereby releasing the suture filament from being captured between the plunger and the housing and allowing movement of the suture filament relative to the plunger and the housing.

Example 27 is the method of any of Examples 19-26, wherein removing the plunger comprises rotating a release tab on the plunger against the housing thereby retracting the plunger from the housing.

Example 28 is the method of any of Examples 19-27, further comprising inserting the suture filament into tissue adjacent a vascular access site.

Example 29 is the method of any of Examples 19-28, wherein inserting the suture filament into the tissue comprises forming a figure-of-eight suture with the suture filament.

Example 30 is the method of any of Examples 19-29, wherein the suture filament when formed into the figure-of-eight comprises two loops and two free ends, and wherein the one or more plunger suture slots comprise a first plunger suture slot disposed in the plunger and a second plunger suture slot disposed in the plunger, and wherein the one or more housing suture slots comprise a first housing suture slot disposed in the housing and a second housing suture slot disposed in the housing, and wherein a first of the two free ends is disposed in the first plunger suture slot and disposed in the first housing suture slot, and wherein a second of the two free ends is disposed in the second plunger suture slot and disposed in the second housing suture slot.

Example 31 is the method of any of Examples 19-30, further comprising coupling the housing to a patient with a substrate coupled to a bottom surface of the housing.

Example 32 is the method of any of Examples 19-31, wherein the substrate is a soft resilient material that prevents or reduces trauma to the patient when the housing is coupled thereto.

Example 33 is the method of any of Examples 19-32, wherein the substrate comprises a therapeutic agent, the method further comprising eluting the therapeutic agent from the substrate into the patient.

Example 34 is the method of any of Examples 19-33, wherein the therapeutic agent comprises a pain reliever for reducing pain, or an antibiotic for reducing infections.

In Example 35, the apparatuses, systems, or methods of any one or any combination of Examples 1-34 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for securing a suture filament, comprising:
   slidably disposing the suture filament into one or more plunger suture slots disposed in a plunger;
   slidably disposing the suture filament into one or more housing suture slots disposed in a housing;
   applying a tension to the suture filament;
   moving the plunger into a channel in the housing so that the one or more plunger suture slots are misaligned with the one or more housing suture slots, thereby capturing the suture filament between the plunger and the housing and preventing movement of the suture filament relative to the plunger and the housing;
   inserting the suture filament into tissue adjacent a vascular access site,
   wherein inserting the suture filament into the tissue comprises forming a figure-of-eight suture with the suture filament,
   wherein the suture filament when formed into the figure-of-eight comprises two loops and two free ends, and
   wherein the one or more plunger suture slots comprise a first plunger suture slot disposed in the plunger and a second plunger suture slot disposed in the plunger, and
   wherein the one or more housing suture slots comprise a first housing suture slot disposed in the housing and a second housing suture slot disposed in the housing, and
   wherein a first of the two free ends is disposed in the first plunger suture slot and disposed in the first housing suture slot, and
   wherein a second of the two free ends is disposed in the second plunger suture slot and disposed in the second housing suture slot; and
   removing the plunger from the plunger channel in the housing thereby aligning the one or more housing suture slots with the one or more plunger suture slots thereby releasing the suture filament from being captured between the plunger and the housing and allowing movement of the suture filament relative to the plunger and the housing,
   wherein removing the plunger comprises pivoting a release tab on the plunger upward and away from a surface of the plunger and rotating the release tab on the plunger against the housing thereby retracting the plunger from the housing.

2. The method of claim 1, further comprising applying a tension to the suture filament and wherein the capturing of the suture filament maintains the tension in the suture filament.

3. The method of claim 1, further comprising cutting the suture filament with a cutter element slidably disposed in a cutter channel in the housing.

4. The method of claim 3, further comprising removing a catheter or a sheath from a blood vessel before cutting the suture filament.

5. The method of claim 3, wherein cutting the suture filament comprises removing a stop element disposed between the cutter element and the housing thereby allowing advancement of the cutter toward the housing to cut the suture filament.

6. The method of claim 3, wherein the two free ends comprise a first free end and a second free end, and wherein the cutting comprises cutting only one of the first free end and the second free end.

7. The method of claim 3, wherein the cutting comprises cutting the suture filament so that it is substantially flush with a bottom wall of the cutter channel in the housing.

8. The method of claim 1, further comprising coupling the housing to a patient with a substrate coupled to a bottom surface of the housing.

9. The method of claim 8, wherein the substrate is a soft resilient material that prevents or reduces trauma to the patient when the housing is coupled thereto.

10. The method of claim 8, wherein the substrate comprises a therapeutic agent, the method further comprising eluting the therapeutic agent from the substrate into the patient.

11. The method of claim 8, wherein the therapeutic agent comprises a pain reliever for reducing pain, or an antibiotic for reducing infections.

\* \* \* \* \*

UNITED STATES PATENT AND TRADEMARK OFFICE
CERTIFICATE OF CORRECTION

PATENT NO. : 12,357,289 B2  
APPLICATION NO. : 18/965484  
DATED : July 15, 2025  
INVENTOR(S) : Subramaniam et al.

Page 1 of 1

It is certified that error appears in the above-identified patent and that said Letters Patent is hereby corrected as shown below:

In the Specification

In Column 4, Line 38, delete "102." and insert --100.-- therefor

In Column 4, Line 62, delete "106" and insert --102-- therefor

In Column 5, Line 51, delete "308" and insert --306-- therefor

In Column 13, Line 6, delete "902" and insert --900-- therefor

In Column 17, Line 31, delete "104" and insert --106-- therefor

In Column 17, Line 43, delete "104" and insert --106-- therefor

In Column 17, Line 45, delete "104" and insert --106-- therefor

In Column 17, Line 60, delete "104" and insert --106-- therefor

In Column 17, Line 62, delete "104," and insert --106,-- therefor

In Column 17, Line 67, delete "104" and insert --106-- therefor

Signed and Sealed this  
Tenth Day of February, 2026

John A. Squires  
*Director of the United States Patent and Trademark Office*